(12) United States Patent
Garry et al.

(10) Patent No.: US 11,000,209 B2
(45) Date of Patent: May 11, 2021

(54) METHOD AND SYSTEM FOR ESTIMATING THE EFFICIENCY OF THE LUNGS OF A PATIENT

(71) Applicant: ROSTRUM MEDICAL INNOVATIONS INC., Vancouver (CA)

(72) Inventors: James Garry, Burnaby (CA); Nathan Ayoubi, Vancouver (CA); Aron Fredrick, Vancouver (CA); Willem J. Atsma, Vancouver (CA); Nicolas Christofi, Vancouver (CA); Hanna McGregor, Surrey (CA)

(73) Assignee: ROSTRUM MEDICAL INNOVATIONS INC., Vancouver (CA)

( * ) Notice: Subject to any disclaimer, the term of this patent is extended or adjusted under 35 U.S.C. 154(b) by 0 days.

(21) Appl. No.: 16/636,773

(22) PCT Filed: Aug. 6, 2018

(86) PCT No.: PCT/CA2018/050957
§ 371 (c)(1),
(2) Date: Feb. 5, 2020

(87) PCT Pub. No.: WO2019/028550
PCT Pub. Date: Feb. 14, 2019

(65) Prior Publication Data
US 2020/0345269 A1    Nov. 5, 2020

Related U.S. Application Data

(60) Provisional application No. 62/542,702, filed on Aug. 8, 2017.

(51) Int. Cl.
*A61B 5/091*  (2006.01)
*A61B 5/08*   (2006.01)
(Continued)

(52) U.S. Cl.
CPC ............ *A61B 5/091* (2013.01); *A61B 5/0059* (2013.01); *A61B 5/082* (2013.01); *A61B 5/087* (2013.01); *A61B 5/0833* (2013.01); *A61B 5/0836* (2013.01)

(58) Field of Classification Search
CPC ....... A61B 5/091; A61B 5/0059; A61B 5/082; A61B 5/0833; A61B 5/0836; A61B 5/087
(Continued)

(56) References Cited

U.S. PATENT DOCUMENTS 4,730,112 A  *  3/1988  Wong ................... G01J 3/4338
                                            250/341.1
5,095,900 A  *  3/1992  Fertig .................. A61B 5/0836
                                            128/205.23
(Continued)

FOREIGN PATENT DOCUMENTS

CA    2379188 A1    2/2001
EP    1024742 A1    8/2000
(Continued)

OTHER PUBLICATIONS

International Search Report and Written Opinion dated Oct. 26, 2018, in corresponding International application No. PCT/CA2018/050957.
(Continued)

*Primary Examiner* — Navin Natnithithadha
(74) *Attorney, Agent, or Firm* — BCF LLP

(57) ABSTRACT

The present disclosure relates to methods and systems for estimating an efficiency of lungs of a patient receiving respiratory care. A blender has a primary input port for receiving a first gas to be delivered to the patient and one or more secondary input ports for receiving a second gas to be delivered to the patient from one or more gas sources. A patient-side port of the blender delivers the first and second
(Continued)

gases to the patient. A gas composition sensor measures a fraction of the first gas and a gas flow sensor measures a flow of the first gas. A controller causes a sequential delivery of the first and second gases to the patient and estimates a functional residual capacity of the patient based on measurements from the gas composition sensor and from the gas flow sensor. The controller may also estimate a cardiac output of the patient.

21 Claims, 14 Drawing Sheets

(51) Int. Cl.
*A61B 5/083* (2006.01)
*A61B 5/087* (2006.01)
*A61B 5/00* (2006.01)

(58) Field of Classification Search
USPC ................................. 600/529, 532, 538
See application file for complete search history.

(56) References Cited

U.S. PATENT DOCUMENTS

| | | | | |
|---|---|---|---|---|
| 5,282,473 A * | 2/1994 | Braig | ............... | A61B 5/083 250/343 |
| 5,570,697 A * | 11/1996 | Walker | ............... | A61B 5/0833 600/532 |
| 5,931,161 A * | 8/1999 | Keilbach | ............... | G01N 21/3504 128/204.22 |
| 6,039,697 A * | 3/2000 | Wilke | ............... | A61B 5/083 250/338.1 |
| 6,306,098 B1 * | 10/2001 | Orr | ............... | A61M 16/0833 128/200.26 |
| 6,648,831 B2 * | 11/2003 | Orr | ............... | A61B 5/029 600/526 |
| 6,908,438 B2 * | 6/2005 | Orr | ............... | A61B 5/029 600/532 |
| 7,335,164 B2 * | 2/2008 | Mace | ............... | A61B 5/083 422/84 |
| 7,686,012 B2 * | 3/2010 | Orr | ............... | A61B 5/0836 128/200.24 |
| 8,096,297 B2 * | 1/2012 | Orr | ............... | A61B 5/029 128/200.24 |
| 10,076,268 B1 * | 9/2018 | Dietrich | ............... | A61B 5/083 |
| 10,449,311 B2 * | 10/2019 | Klein | ............... | A61M 16/12 |
| 2001/0031928 A1 * | 10/2001 | Orr | ............... | A61B 5/029 600/526 |
| 2004/0049113 A1 * | 3/2004 | Orr | ............... | A61M 16/0833 600/481 |
| 2004/0145743 A1 * | 7/2004 | Wilson | ............... | G01N 21/3504 356/437 |
| 2005/0203432 A1 * | 9/2005 | Orr | ............... | A61M 16/0833 600/532 |
| 2010/0132710 A1 * | 6/2010 | Orr | ............... | A61M 16/0045 128/205.17 |
| 2013/0109978 A1 * | 5/2013 | Fisher | ............... | A61B 5/7278 600/484 |
| 2014/0311491 A1 * | 10/2014 | Klein | ............... | A61M 16/12 128/204.22 |
| 2015/0114394 A1 * | 4/2015 | Klein | ............... | A61M 16/0066 128/203.25 |
| 2016/0158481 A1 | 6/2016 | Klein et al. | | |
| 2017/0224230 A1 * | 8/2017 | Fisher | ............... | A61B 5/7225 |
| 2017/0361042 A1 * | 12/2017 | Klein | ............... | A61M 16/026 |
| 2018/0311454 A1 * | 11/2018 | Klein | ............... | A61M 16/1005 |
| 2018/0353083 A1 * | 12/2018 | Fisher | ............... | A61B 5/0205 |
| 2019/0099082 A1 * | 4/2019 | Jutte | ............... | A61B 5/0075 |

FOREIGN PATENT DOCUMENTS

| | | |
|---|---|---|
| WO | 200473482 A2 | 9/2004 |
| WO | 2011143751 A1 | 11/2011 |
| WO | 2015145115 A1 | 10/2015 |

OTHER PUBLICATIONS

Elkayam et al., "Non-invasive measurement of cardiac output by a single breath constant expiratory technique", Thorax, vol. 39, No. 2, Feb. 1, 1984, p. 107-113.
Brewer, "Noninvasice partial rebreathing cardiac output for nonintubated subjects", Aug. 1, 2001, retrieved from the Internet: https://medicine.utah.edu/anesthesiology/abl/theses/brewermasterthesis.pdf.
Supplementary European Search Report issued in corresponding European patent application No. 1884458.4 and dated Nov. 4, 2020.
Tehrani et al., "A dual closed-loop control system for mechanical ventilation", Journal of clinical monitoring and computing, Apr. 1, 2004.
Tehrani et al., "A closed-loop system for control of the fraction of inspired oxygen and the positive end-expiratory pressure in mechanical ventilation", Computers in Biology and Medicine, vol. 42, No. 11, Nov. 1, 2012, p. 1150-1156.
Fisher et al., Sequential gas delivery provides precise control of alveolar gas exchange, Respiratory Physiology and Neurobiology, Elsevier, vol. 225, Feb. 1, 2016, p. 60-69.

* cited by examiner

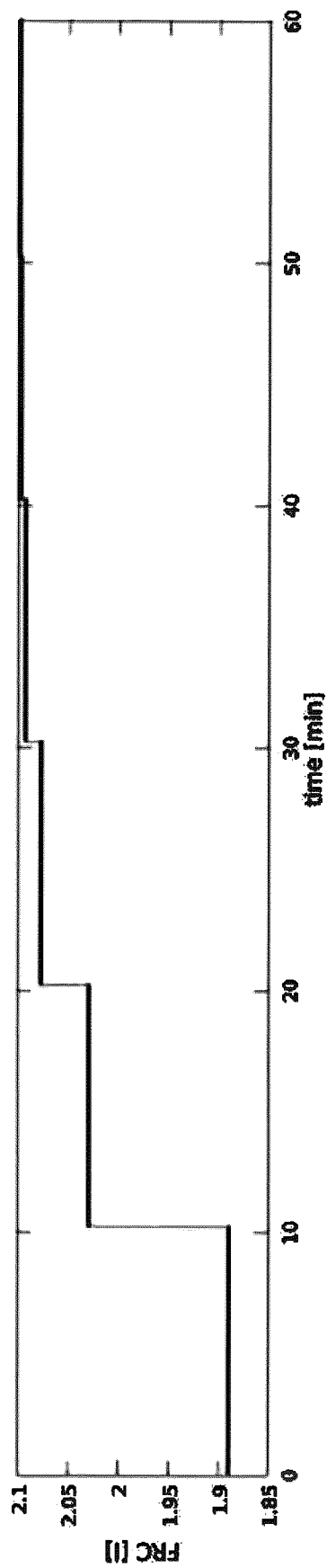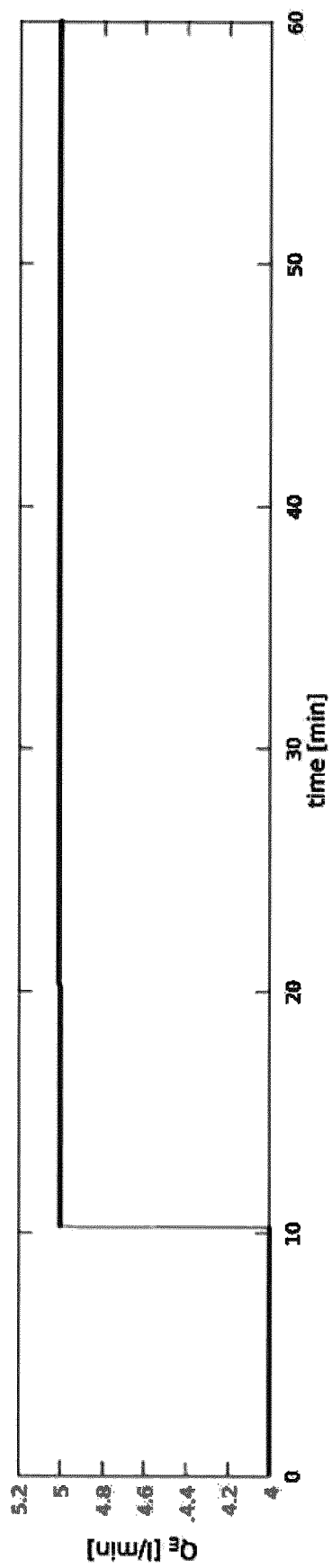

METHOD AND SYSTEM FOR ESTIMATING THE EFFICIENCY OF THE LUNGS OF A PATIENT

TECHNICAL FIELD

The present disclosure relates to the field of respiratory care. More specifically, the present disclosure relates to a method and a system for estimating the efficiency of the lungs of a patient.

BACKGROUND

Sequential gas delivery (SGD) is a technique used to deliver a well-controlled amount of inspiratory gas to the alveolar space of a patient under respiratory care, whether the patient is breathing spontaneously or under assistance from a mechanical ventilator. The use of SGD allows the establishment of a constant gradient between inspired gas in the alveolar space of the patient and the blood circulating in the pulmonary capillary bed.

Sequential Gas Delivery divides each breath in two volumes: a first volume $V_{G1}$ containing gas 1 (G1) and a second volume $V_{G2}$ containing gas 2 (G2), which is composed such that it is a neutral gas for exchange with the capillary bed and a gas g of interest. Gas 1 (G1) is delivered in a first part of a breath and its volume (or flow rate) is set such that all of G1 will reside inside the alveolar space and participate in gas exchange with the capillary bed. The balance of each breath is supplied with G2. To determine a concentration $F_{G2}$ of G2, it is set to the end-tidal concentration $F_{ET}$ of a most recent breath.

Recent applications of SGD combined with an iterative algorithm have resulted in systems that are guaranteed to restore steady-state after a limited number of iterations. Current SGD techniques use the inherent dynamics of these systems to alternate between estimation of a cardiac output (CO) and a concentration of inspired gas ($F_{G1}$).

Current SGD systems are slow to, or do not at all, evaluate the functional residual capacity (FRC) of patients receiving respiratory care. These systems require multiple iterations of their algorithms to accurately determine the cardiac output of a patient.

Improvements are needed so that volumes (or flows) and concentration of supplied gases are adapted to the needs of each individual patient under respiratory care.

SUMMARY

According to the present disclosure, there is provided a method for estimating an efficiency of lungs of a patient receiving respiratory care, comprising:
   a) causing a delivery of a first gas in a first breath to the patient at a perturbative concentration;
   b) after a), determining an end-tidal concentration of the patient based on measurements obtained during exhalation of the first breath of the patient;
   c) recalculating a concentration of the first gas for delivery to the patient in a following breath based at least in part on a variation of the end-tidal concentration of the patient between a preceding breath and a current breath;
   d) determining an updated end-tidal concentration of the patient based on measurements obtained during exhalation after c);
   e) repeating c) and d) until at least one of:
      i) a predetermined time duration after a) elapses,
      ii) a predetermined number of breaths have passed after a), and
      iii) at least two successive updated end-tidal concentration values are substantially equal; and
   f) after e), estimating a functional residual capacity (FRC) of the patient.

According to the present disclosure, there is also provided a system for estimating an efficiency of lungs of a patient receiving respiratory care, comprising:
   at least one gas source;
   a blender having a primary input port adapted to receive a first gas to be delivered to the patient and at least one secondary input port adapted to receive a second gas from a corresponding one of the at least one gas source, the blender further having a patient-side port adapted for delivery of the first gas and of the second gas from the at least one gas source toward the patient;
   a gas composition sensor adapted to measure a fraction of the first gas;
   a gas flow sensor adapted to measure a flow of the first gas; and
   a controller operatively connected to the at least one gas source, to the gas composition sensor and to the gas flow sensor, the controller being adapted to:
      sequentially deliver the first and second gases to the patient, and
      estimate a functional residual capacity (FRC) of the patient based on measurements from the gas composition sensor and from the gas flow sensor.

The present disclosure further provides a method for estimating an efficiency of lungs of a patient receiving respiratory care, comprising:
   a) causing a delivery of a first gas in a first breath to the patient at a perturbative concentration;
   b) after a), determining an end-tidal concentration of the patient based on measurements obtained during exhalation of the first breath of the patient;
   c) recalculating a concentration of the first gas for delivery to the patient in a following breath based at least in part on a variation of the end-tidal concentration of the patient between a preceding breath and a current breath;
   d) determining an updated end-tidal concentration of the patient based on measurements obtained during exhalation after c);
   e) repeating c) and d) until at least one of:
      i) a predetermined time duration after a) elapses,
      ii) a predetermined number of breaths have passed after a), and
      iii) at least two successive updated end-tidal concentration values are substantially equal; and
   f) after e), estimating a cardiac output (CO) of the patient.

The present disclosure also provides a method for estimating an efficiency of lungs of a patient receiving respiratory care, comprising:
   a) causing a delivery of a first gas in a first breath to the patient at a perturbative concentration;
   b) after a), determining an end-tidal concentration of the patient based on measurements obtained during exhalation of the first breath of the patient;
   c) recalculating a concentration of the first gas for delivery to the patient in a following breath based at least in part on a variation of the end-tidal concentration of the patient between a preceding breath and a current breath;

d) determining an updated end-tidal concentration of the patient based on measurements obtained during exhalation after c);
e) repeating c) and d) until at least one of:
   i) a predetermined time duration after a) elapses,
   ii) a predetermined number of breaths have passed after a), and
   iii) at least two successive updated end-tidal concentration values are substantially equal; and
f) after e), estimating a mixed venous gas content of the patient.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which:

FIGS. 8a to 8d show 5 successive iterations of the algorithm;

Like numerals represent like features on the various drawings.

DETAILED DESCRIPTION

Figure 1:
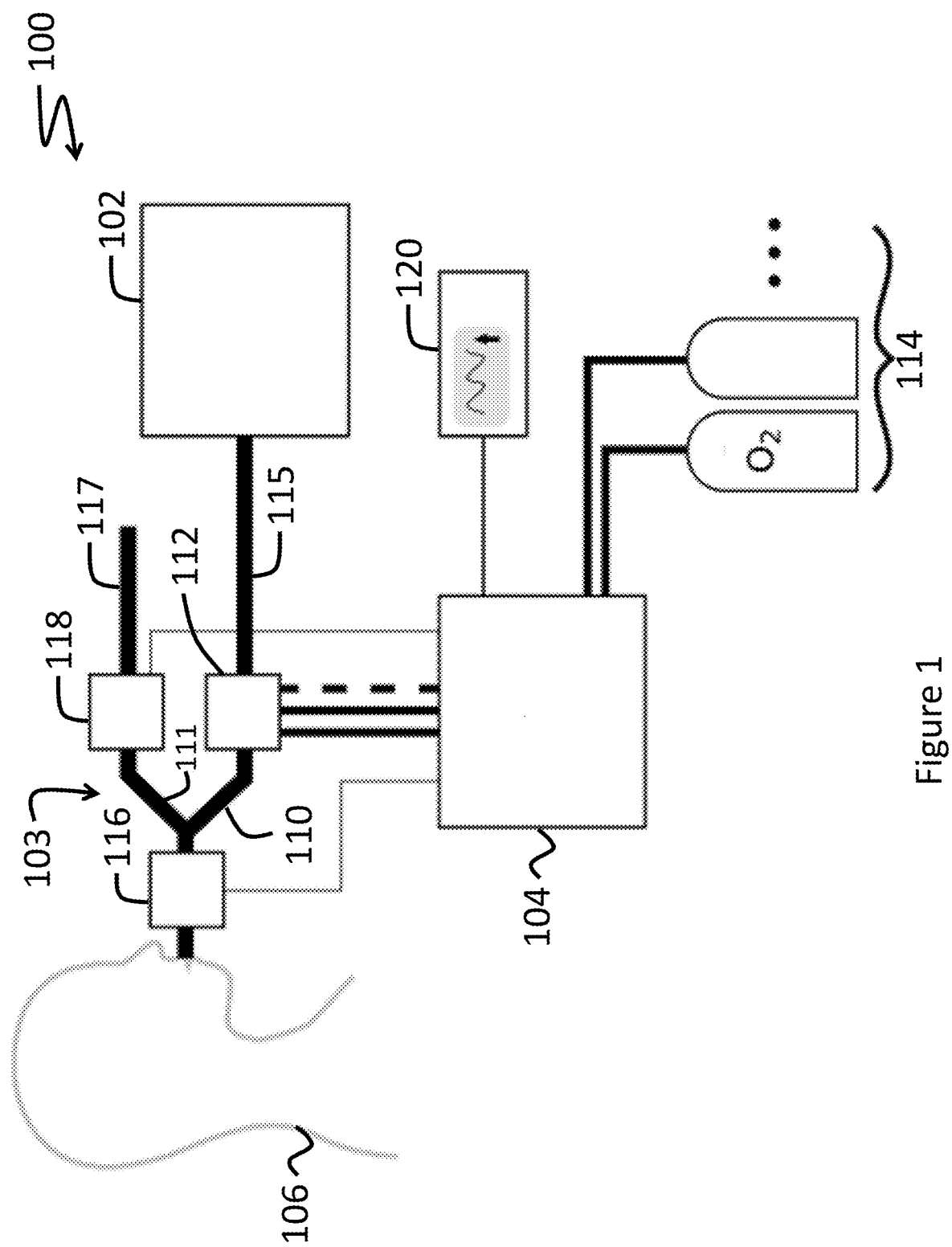
FIG. 1 shows a schematic diagram of a system implementing a titration method according to an embodiment.

Various aspects of the present disclosure generally address one or more of the problems related to the number of iterations required by current sequential gas delivery systems to properly evaluate the functional residual capacity (FRC), cardiac output (CO) and mixed venous gas content ($C_{\bar{v}}$) of patients under respiratory care and to the titration of volumes (or flows) and concentration of supplied gases that should be adapted to the needs of each individual patient under respiratory care.

The present disclosure introduces a method and a system for non-invasive measurement of lung efficiency. The disclosed system manipulates gases, volumes and/or flows of the gases, and duration of delivery of the gases in ventilated patients in order to determine specific characteristics indicative of the overall efficiency of ventilation. Measurements are based on quantities determined from inspired and expired air. In an embodiment, the measurement principle relies on the differential Fick equation and allows to rapidly re-establish steady-state gas delivery after a perturbation. The system may estimate the Functional Residual Capacity (FRC) of the lungs of a patient without performing wash-out trials or requiring uncommon or expensive gases. The system may provide an estimate of perfusion of the lungs of the patient and of delivered oxygen.

In the context of the present disclosure, the term "gas" is not limited to gases consisting of any single element or compound. Terms such as "a gas", "the gas", "challenge gas", "first gas" and "second gas" may each refer to a single gas, for example oxygen, carbon dioxide, and the like, or to a mixture or blend of gases, for example and without limitation respiratory air.

The present technology is intended to be used for assisting patients under respiratory care, whether a patient is breathing spontaneously or under assistance from a mechanical ventilator. In the latter case, the information supplied by the system may be used to assist in the titration of ventilator settings for the needs of each individual patient. Specific embodiments may be directed to the ventilation of compromised lungs.

Context

The present technology relies on the concept of Sequential Gas Delivery (SGD) to deliver a well-controlled amount of inspired gas to the alveolar space of a patient.

The CO estimate is a consequence of the difference in breath make-up, when the patient has reached a steady-state with respect to the make up of the air in their lungs. The detection of steady-state happens when the patient's end-tidal breaths stop changing. Starting from that point, the estimation of cardiac output (which may be estimated continuously) in the absence of significant shunt provides an accurate reflection of the actual blood flow. CO can be measured in a non-invasive manner using the differential Fick equation. The differential Fick equation can be written as in equation (1):

$$\dot{Q}_E = \frac{\dot{V}_g^B - \dot{V}_g^T}{F_{dis}(P_{ETg}^T) - F_{dis}(P_{ETg}^B)} \tag{1}$$

In equation (1), $\dot{Q}_E$ is the estimate of the CO; $\dot{V}_g$ is the amount of a gas g breathed out; $P_{ETg}$ is the partial pressure of end-tidal pressure of a gas g as determined by the concentration of the gas g; $F_{dis}(P_g)$ is the dissociation curve for gas g; superscripts B and T indicate baseline and test measurements respectively.

Each measurement is made using the provision to the patient of a known amount of gas in an inhaled breath, followed by the subsequent inhalations such that a stable state of gas-exchange occurs. As long as baseline and test measurements are performed with the cardio-pulmonary system in steady-state with CO and the mixed venous gas content ($C_{\bar{v}}$) is stable, equation (1) provides an estimate of the pulmonary blood flow. In general the 'Test' measurement requires the patient to inhale a raised concentration of some soluble gas, perturbing the make-up of blood flowing from the lung. If the measurement is completed before the blood returns to the lung, then the mixed venous gas content ($C_{\bar{v}}$) of the perturbing gas can be assumed to be constant. The actual amount may vary from patient to patient and may be altered by their physiological state over long periods. However, even ailing patients have essentially stable blood gas content over the spans of time considered here, generally in the order of about 20 seconds.

It may be observed that in the above and in subsequent discussions, measurements may be corrected to Body Temperature, Pressure, Saturated (BTPS), as they would be in the lungs. In addition, assuming the gas g is $CO_2$ the dissociation function $F_{dis}()$ includes compensations such as the Haldane effect and known influences. In the following discussion, in order to simplify the present disclosure, the subscript g is not shown when discussing the pressure, volume, fraction or like parameter of a specific gas. Examples provided below are based on the use of $CO_2$ alone, but the use of other gases or of combinations of gases is also contemplated.

The present technology introduces a system and a method that use SGD to control the gradient between alveolar space and the capillary bed. It uses a method to estimate the Functional Residual Capacity (FRC), Cardiac Output ($\dot{Q}_E$), mixed venous gas content ($C_{\bar{v}}$) and a method for measuring oxygen consumption ($VO_2$) or for measuring any gas of interest. The system may be used to assist a spontaneously breathing patient by the supply of one or more challenge gases to modify the make-up of ambient air breathed by the patient. The system may alternatively be attached to the airway of an existing mechanical ventilator, in which case the system does not directly control that device's operation but rather modifies the make-up of the air delivered by the mechanical ventilator to the patient without changing the breathing rate or tidal volume.

System for Estimating the Efficiency of the Lungs of a Patient

Figure 2:
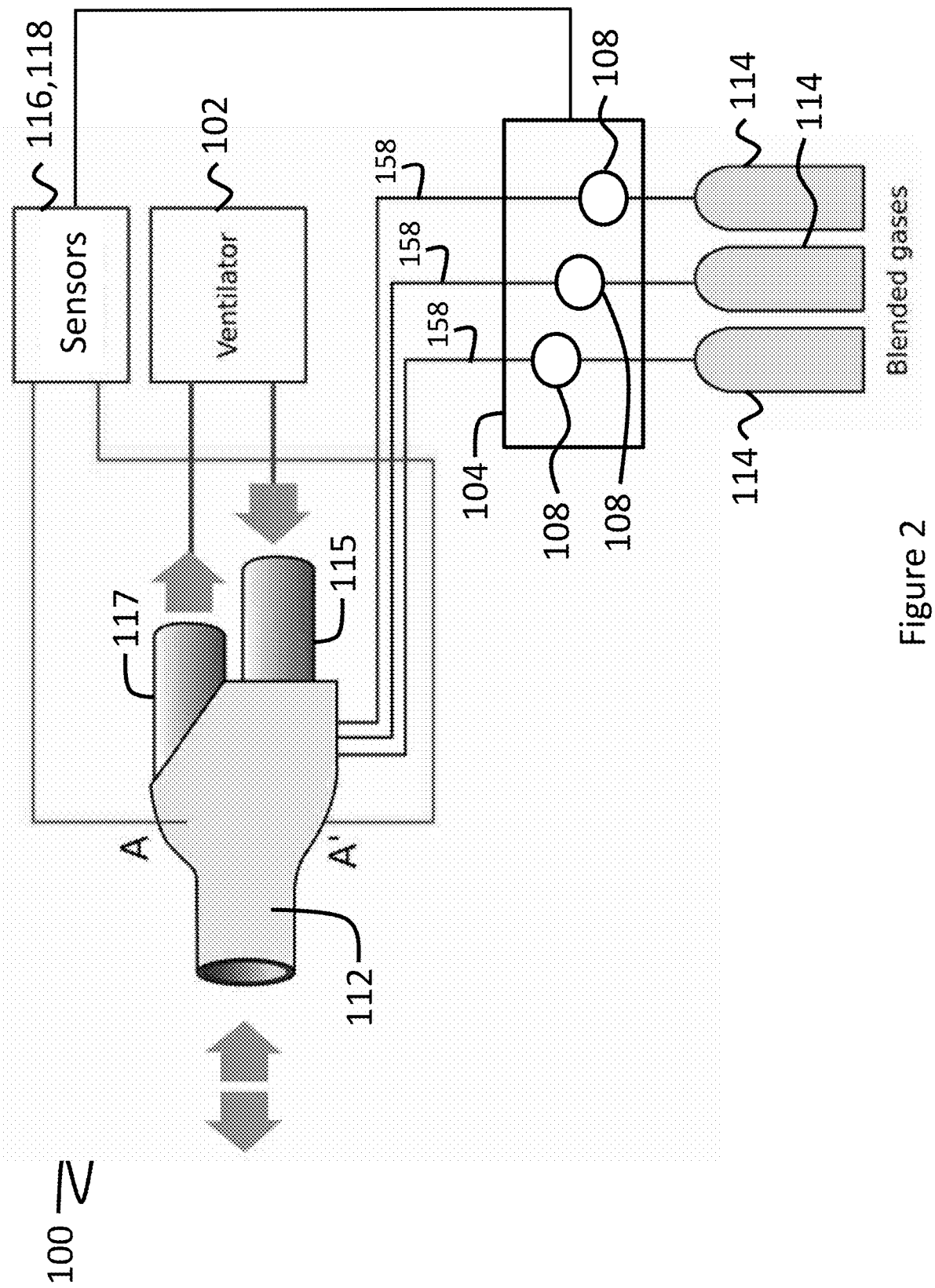
FIG. 2 shows additional details of the system of FIG. 1.

Referring now to the drawings, FIG. 1 shows a schematic diagram of a system 100 implementing a titration method according to an embodiment in view of estimating the efficiency of the lungs of a patient. FIG. 2 shows additional details of the system of FIG. 1. Referring at once to FIGS. 1 and 2, a mechanical ventilator 102 and a controller 104 are joined by a common respiratory airway circuit 103 to direct gases to and from the mouth of a patient 106 under respiratory care. The controller 104 includes internal valves 108 to control delivery of gases to an inhale limb 110 of the common respiratory airway circuit 103 using a blender 112 that mixes one or more challenge gases from corresponding one or more challenge gas sources 114 into an airstream provided in an inspiratory conduit 115 that provides a fluid connection between the mechanical ventilator 102 and the blender 112. In the context of the present disclosure, the term "challenge gas" is meant to designate a gas or a combination of gases added to a respiratory gas using a SGD technique.

The mechanical ventilator 102 is not an essential component of the system 100. The system 100 may also be used when the patient 106 is spontaneously breathing, in which case the inspiratory conduit 155 may be open to ambient air.

Gases exhaled by the patient 106 may be expelled through an exhale limb 111 and further through an exhaust conduit 117. The overall make-up of inhaled and exhaled gases is monitored near the mouth of the patient 106 using a gas composition sensor 116, and a gas flow sensor 118. Although the gas flow sensor 118 as shown on FIG. 1 is mounted between the exhale limb 111 and the exhaust conduit 117, positioning of one or more gas flow sensors on other parts of the system 100 is also contemplated. The controller 104 may integrate over time, for example over an inspiratory period of the patient 106, a gas flow measured by the gas flow sensor 118 in order to determine a volume of a gas delivered to the patient. Gas volumes may also be measured or calculated based on a construction of the various components of the system 100 and based on gas pressures.

Various physiological parameters from the gas composition sensor 116 and from the gas flow sensor 118 are shown on a display device of operator interface 120 connected to the controller 104.

It is beneficial that the elements where the gases are blended should have minimal volumes, so that the patient is ventilated with well-described mixtures that do not undergo unnecessary dilution in the shared spaces of the common respiratory airway circuit 103. The system encompasses a design for a gas blender (d) that has such a restricted common volume without impeding airflow through it. Non-limiting example implementations of the blender 112 are provided on FIGS. 3 and 4.

Figure 3A:
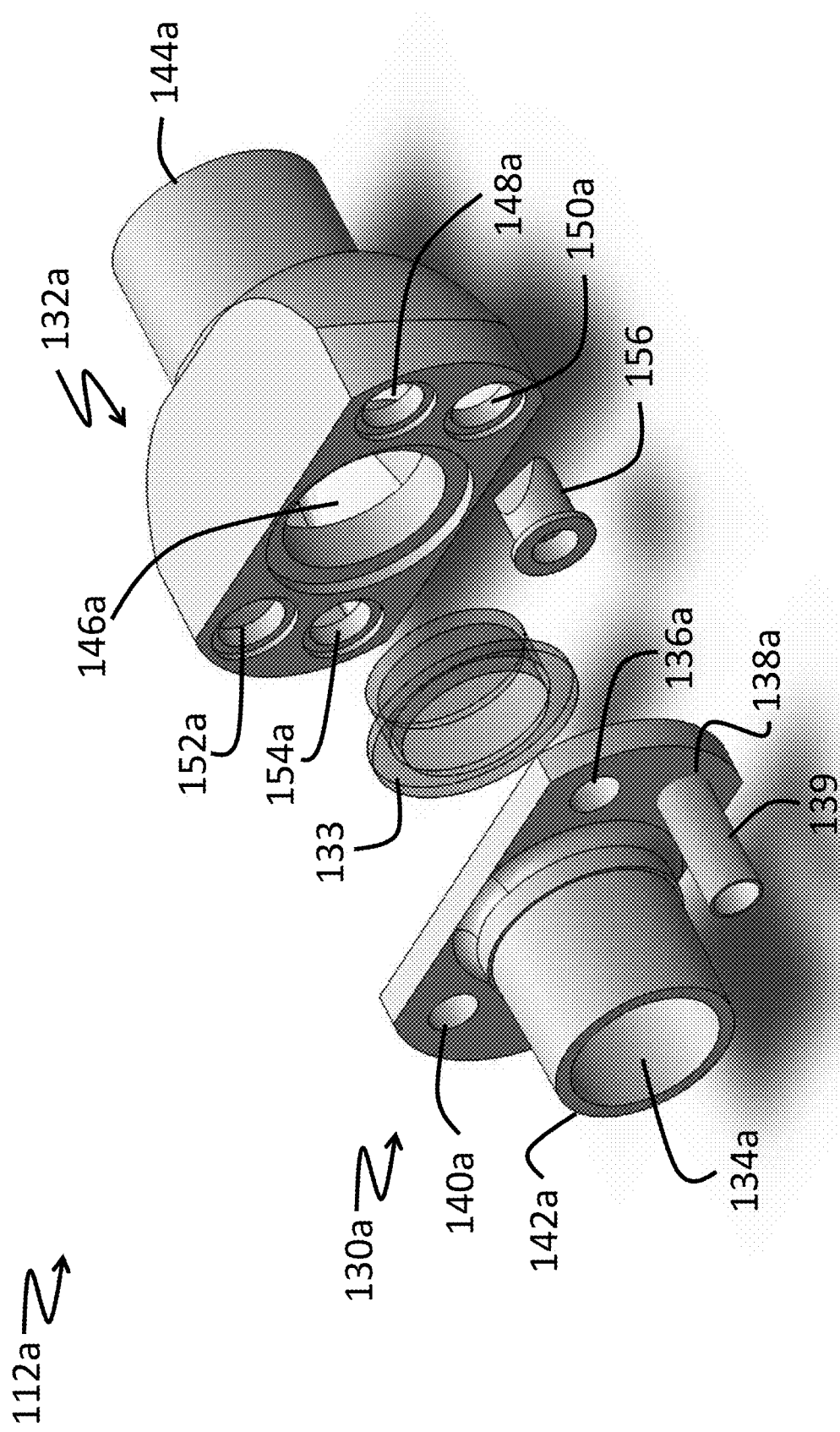
FIG. 3a shows an exploded view of a first example of a blender being part of the system of FIG. 1.

FIG. 3a shows an exploded view of a first example of a blender 112 being part of the system of FIG. 1. A blender 112a includes an input side 130a and an output side 132a. The input side 130a includes a relatively large primary input port 134a and, in a non-limiting example, four (4) smaller secondary input ports 136a, 138a, 140a and 142a (the secondary input port 142a being hidden from view behind the primary input port 134a on FIG. 3a). The primary input port 134a may be fluidly connected to the mechanical ventilator 102, when present, or may directly receive ambient air from the atmosphere. Although only one is shown, a connecting conduit 139 may be attached to each of the secondary input ports 136a, 138a, 140a and 142a. The output side 132a includes a relatively large patient-side port 144a, an internal mixing chamber 146a and four (4) internal conduits 148a, 150a, 152a and 154a that connect to the respective secondary input ports 136a, 138a, 140a and 142a. Sleeves 156 may be used as interfaces between the respective secondary input ports and internal conduits; the sleeves 156 are not externally visible when the blender 112a is assembled by joining the input side 130a to the output side 132a. An optional one-way valve 133 may be inserted between the input side 130a and the output side 132a. Respiratory gas are received at the blender 112a via a large caliber inspiratory conduit 115 (shown on FIG. 1) open to the ambient air or connecting the mechanical ventilator 102 to the primary input port 134a. Challenge gases from up to four (4) challenge gas sources 114 are received at the blender 112a via up to four (4) smaller caliber conduits (three (3) such conduits 158 are shown on FIG. 2) connecting the challenge gas sources 114 via the controller 104, to a connection tube 139 mounted to each of the secondary input ports 136a, 138a, 140a and 142a. Although only one is shown, a respective connection tube 139 may be attached to each of the secondary input ports 136a, 138a, 140a and 142a to facilitate attachment of the conduits 158. The respiratory gas and the challenge gases are mixed in the mixing chamber 146a and expelled via the patient-side port 144a into the common respiratory airway circuit 104 of FIG. 1. The mixing chamber 146a is sized and configured to minimize any dead space added by the blender 112a to the respiratory airway circuit 103, for example between the mechanical ventilator 102 and the mouth of the patient 106.

Figure 3B:
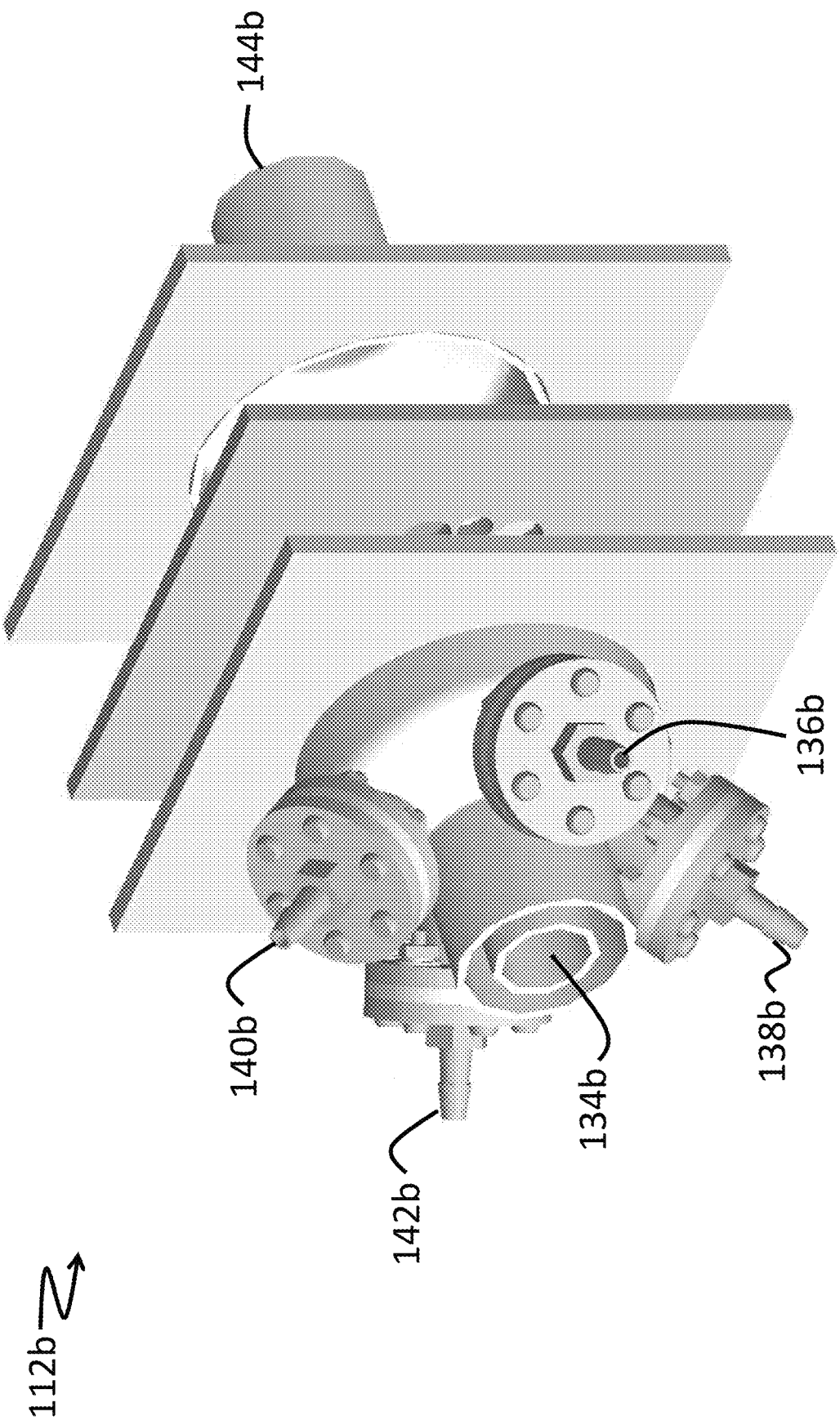
FIG. 3b shows an exploded view of a second example of a blender being part of the system of FIG. 1.

FIG. 3b shows an exploded view of a second example of a blender being part of the system of FIG. 1. A blender 112b includes a primary input port 134b and a patient-side port 144b. The blender 112b differs from the blender 112a primarily in the construction, shape and orientation of secondary input ports 136b, 138b, 140b and 142b, but otherwise implement the same or equivalent features as those of the blender 112a.

Figure 3C:
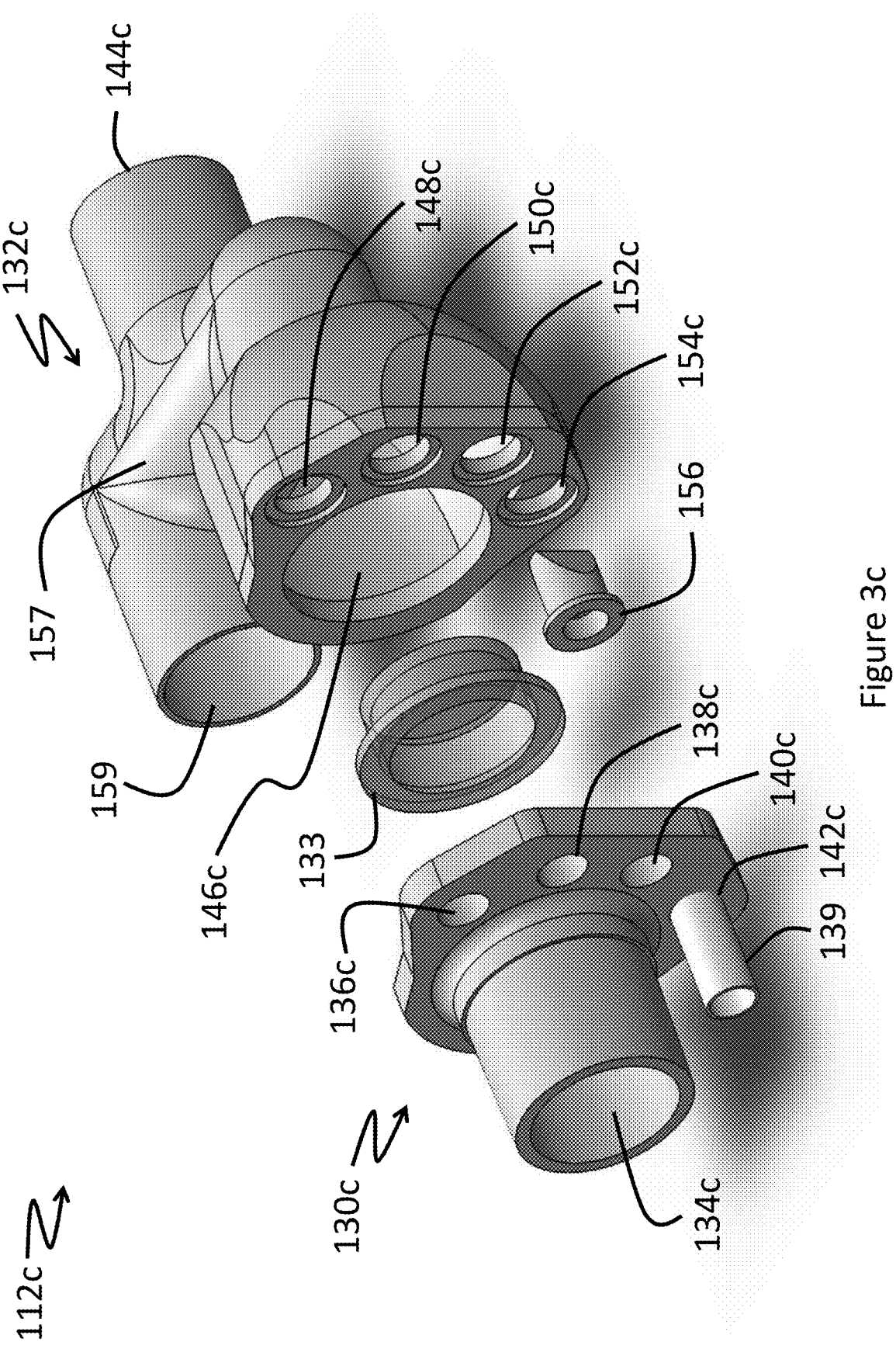
FIG. 3c shows an exploded view of a third example of a blender being part of the system of FIG. 1.

The blender 112a or 112b or any other implementation of the blender 112 may be integrated in a Y-shaped configuration as illustrated on FIG. 2. For example, FIG. 3c shows an exploded view of a third example of a blender being part of the system of FIG. 1. A blender 112c generally implements the same or equivalent features as those of the blenders 112a and 112b. The blender 112c comprises an input side 130c and an input/output side 132c. An input port 134c, secondary input ports 136c, 138c, 140c and 142c, internal conduits 148c, 150c, 152c and 154c and a mixing chamber 146c perform the same functions as described for comparable features of the blenders 112a and 112b. On the input/output side 132c, a patient-side port 144c is bidirectional for passing inhale and exhale gases to and from the patient 106. An internal bifurcation of the input/output side 132c, generally at 157, allows separating the inhale and exhale gases. The internal bifurcation 157 embodies at least in part a variant of the common respiratory airway circuit 103 of FIG. 1. The inhale gases are directed from the mixing chamber 146c toward the patient 106 by the input/patient-side port 144c, generally in the same manner as in the case of the blenders 112a and 112b. Exhale gases from the patient 106 are expelled through an exhaust port 159 that may be connected to the exhaust conduit 117 of FIGS. 1 and 2. Alternatively, the exhaust port 159 may directly expel the exhale gases to the atmosphere. The optional one-way valve 133, if present, may prevent exhale gases from being expelled through the input port 134c.

Figure 4:
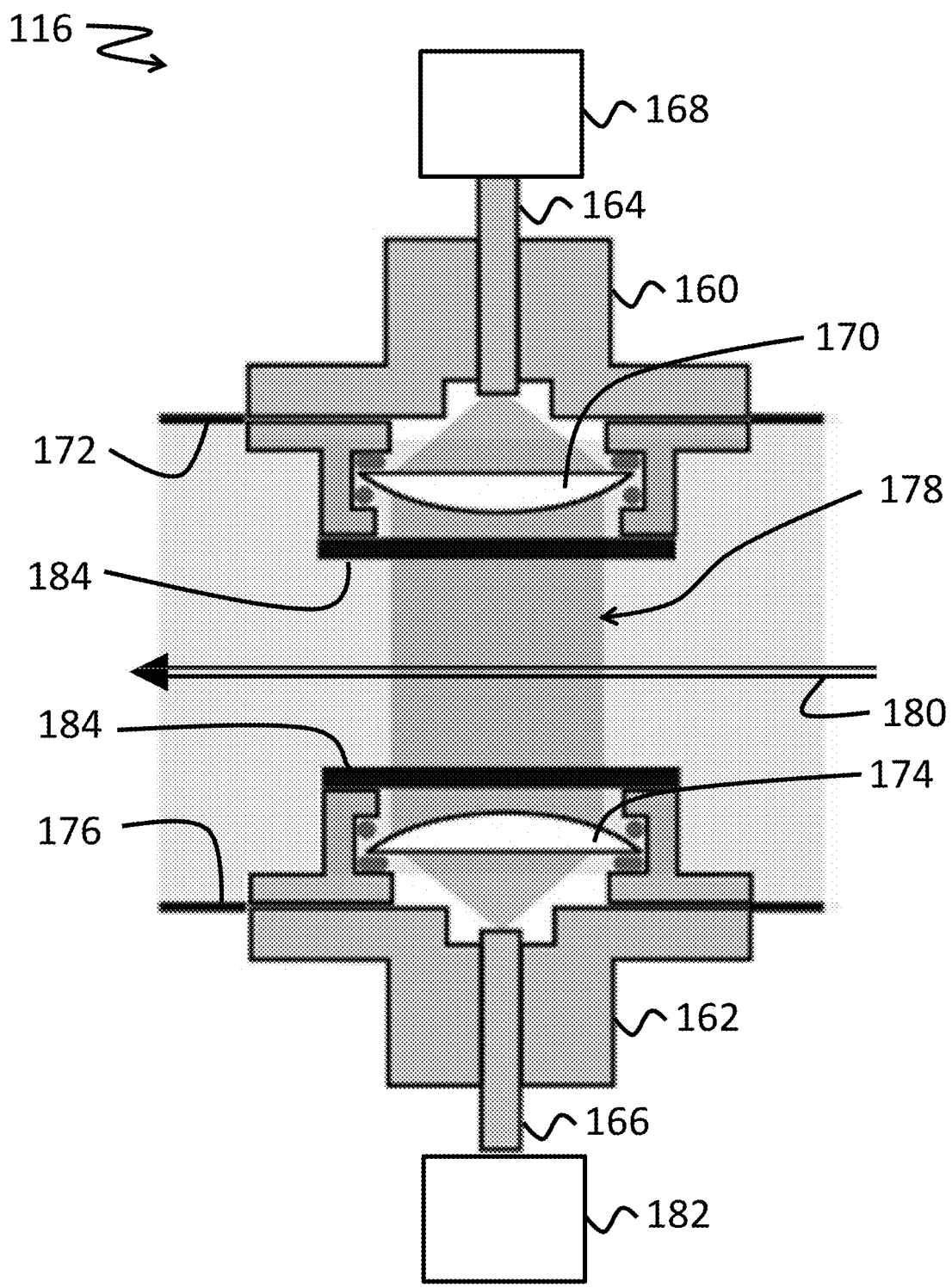
FIG. 4 is a schematic diagram of a gas composition sensor according to an embodiment.

FIG. 4 is a schematic diagram of a gas composition sensor 116 according to an embodiment. FIG. 4 is not to scale. The gas composition sensor 116 may be mounted on the blender 112 (on either variants 112a or 112b of the blender, or on any equivalent blender 112), for example along a line identified as A-A' on FIG. 2. The gas composition sensor 116 comprises a first coupling 160 and a second coupling 162 that are both mounted on the patient-side port 144a or 144b of the blender 112. The first and second couplings 160, 162 are adapted for attachment of respective first and second external optical fibers 164 and 166. A light source 168 illuminates the first external optical fibers 164. A first lens 170 is mounted on a first internal face 172 of the patient-side port 144a, 144b or 144c of the blender 112. The first lens 170 is positioned to be illuminated by the first external optical fiber 164. A second lens 174 is mounted on a second internal face 176 of the patient-side port 144a, 144b or 144c of the blender 112. The second lens 174 is positioned opposite from the first lens 170 so that light 178 emitted by the first lens 170 through a flow 180 formed of the first and second gases before being received at the second lens 174 to illuminate the second external optical fiber 166. A spectroscopic analyzer 182 receives light from the second external optical fibers 174 and to provides measurements of the composition of the flow 180, for example a measure of the fraction of the first gas, to the controller 104.

Windows 184 may be included in the gas composition sensors in order to protect the first and second lenses 170 and 174 from condensation and any impurities that may reside in the flow 180 and to facilitate cleaning of the gas composition sensor 116.

Although the flow 180 is shown as being unidirectional on FIG. 4, the gas composition sensor 116 may be adapted to measure the composition of a bidirectional flow. Additionally, the use of distinct gas composition sensors mounted on the inhale limb 110 of the common respiratory airway circuit 103, on the inspiratory conduit 115, on the exhale limb 111 and/or on the exhaust conduit 117 is also contemplated.

FIGS. 5a to 5f are views of a gas flow sensor 118 according to an embodiment. None of FIGS. 5a to 5f is to scale. In a non-limiting embodiment, the gas flow sensor 118 mounted on a conduit 188, for example the inhale limb 110, the exhale limb 117, or the patient-side port 144a, 144b or 144c of the blender 112, includes a light source 190, which may be a directional light source such as for example a laser, a one-way valve 192 adapted to block a gas flow in a reverse direction and to flex under a forward direction 194 of the gas flow. The one-way valve 192 to deflects light 196 emitted by light source 190 when flexed. The gas flow sensor 118 also includes a light detector 198. The light detector 198 is positioned so that flexing of the one-way valve 192 modifies a detection of the light emitted by the light source 190.

Figure 5:
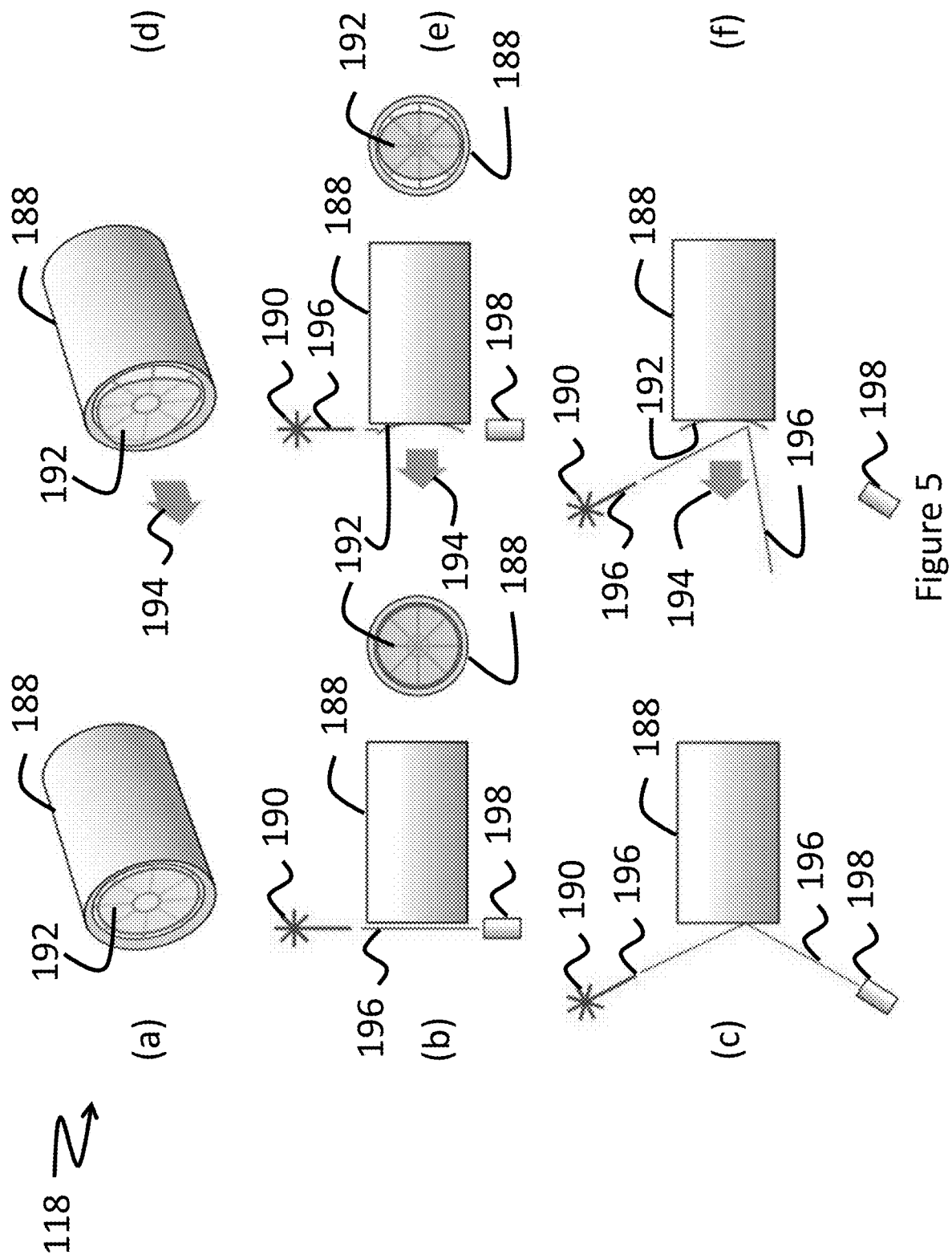
FIGS. 5a to 5f are views of a gas flow sensor according to an embodiment.

In more details FIG. 5a shows the gas flow sensor 118 in a 'no flow' condition, when there is no pressure in the gas flow sensor 118 or when the one-way valve 192 blocks any reverse gas flow that could otherwise be caused by current pressure conditions in the absence of the one-way valve 192. FIG. 5b illustrates a first variant in which the light 196 from the light source 190 directly reaches a first light detector 198, being unhindered by the one-way valve 192. FIG. 5c shows a second variant in which the light source 190 is positioned so that the light 196 from the light source 190 impinges on the one-way valve 192, being reflected at an angle by a reflective surface of the one-way valve 192 toward the light detector 198.

FIG. 5d shows that the one-way valve 192 flexes to allow flow of gas in the forward direction 194. FIG. 5e shows that, in the variant of FIG. 5b, flexing of the one-way valve 192 causes blocking of the light 196, which no longer reaches the light detector 198. FIG. 5f shows that, in the variant of FIG. 5c, flexing of the one-way valve 192 causes the light 196 to be reflected at another angle so that it no longer reaches the light detector 198.

Virtual Inhaled Gas Fraction

The system is based on the concept of "virtual inhaled gas fraction". A "virtual inhaled gas concentration" may be defined as the imaginary concentration of the inhaled gas in the alveolar space after inhalation is complete and before gas exchange with the capillary bed has occurred. This is a virtual quantity because gas exchange between the alveolar space and the capillary bed happens continuously. As the patient breathes out, new blood is pumped into the capillary bed having a partial pressure that is not equilibrated yet and therefore the gradient between the alveolar space and the capillary bed is updated continuously.

The concept of a virtual inhaled gas fraction is nonetheless useful and analogous to the use of end-tidal gas fraction. The present technology uses the end of exhalation as a virtual synchronization point between mass transport from the lungs of the patient with the environment and from the lungs with the capillary bed.

The alveolar volume for a given breath is defined according to equation (2):

$$V_A = V_{G1} + V_{G2} + FRC \qquad (2)$$

In equation (2), $V_{G1}$ and $V_{G2}$ are the sequential gas delivery (SGD) gas volumes for a first gas (gas 1, or G1) and a second gas (gas 2, or G2), and FRC is the Functional Residual Capacity. A first mixture G1 and of G2 is delivered in a first phase of the given breath of the patient. A second mixture of G1 and of G2 is delivered in a second phase of the given breath of the patient. The first and second mixtures may each include distinct volumes and/or blends of G1 and of G2. Note that for convenience, $V_{G2}$ is defined such that it does not include anatomical dead space volume ($V_{DA}$).

Tidal volume $V_t$ is defined according to equation (3):

$$V_t = V_{G1} + V_{G2} + V_{DA} \quad (3)$$

The "virtual inhaled gas fraction $F_{AI}$" is defined as the imagined gas fraction in the alveolar space after inhale but before gas exchange with the capillary bed takes place. At a breath k the virtual alveolar gas fraction is estimated using equation (4):

$$F_{AI}^k = \frac{V_{G1} \cdot F_{G1}^k + V_{G2L}^k F_{G2}^k + V_{FRC} \cdot F_A^{k-1}}{V_A^k} \quad (4)$$

Setting $F_A = F_{G2} = F_{ET}$, equation (4) simplifies to equation (5):

$$F_{AI}^k = \frac{V_{G1} \cdot F_{G1}^k + (V_{G2L}^k + V_{FRC}) \cdot F_{ET}^{k-1}}{V_A^k} \quad (5)$$

Equation (5) expresses the amount of gas available in the alveolar space. Because the diffusion process between the capillary bed and alveolar space is fast compared to the breathing rate, it may be assumed that when the patient exhales, the alveolar gas will have equilibrated with blood in the capillary bed until no partial pressure gradient remains. In equations (4) and (5), the term $V_{G2L}^k$ may be described as a part of the second gas G2 that may, through diffusion or some other process, undergo gas-exchange with the pulmonary bed. $V_{G2L}^k$ therefore designates a volume of the gas G2 in the live space. The subscript L refers to a quantity (a volume, in this case) that can play a role in the exchange of gas into the bloodstream. Such volumes are termed as 'Live' to distinguish them from 'Dead' volumes that are unable to contact the perfusing blood.

It may be noted that the FRC is large compared to the tidal volume. A change in G1 will result in a change in $F_{AI}$ that is only a fraction of the change in $F_{G1}$.

Single Step Return to Steady-State

In an application of the differential Fick method for estimation of cardiac output, the two measurements of $\dot{V}_{CO_2}$ are performed during steady state. The two measurements are then used with Equation (1) to produce the estimate. Within the context of the present disclosure, the term steady-state may be understood as expressing that the mixed venous gas content (CO is constant and that the alveolar concentration $F_{AI}$ is constant from one breath to the next.

Condition a) is met if the measurements can be completed before the blood completes a circulation (typically 20 seconds or more in an adult). Condition b) is assumed to be met when $F_{ET}$ is constant. It is desired to return the patient to a steady-state within about 4 breaths, the first of which is the initial perturbation. If the FRC is known, the patient may be caused to return to steady-state within a single breath.

During a baseline, steady state is assumed. Denoting baseline operation with the superscript B and dropping the index k:

$$F_{AI}^B = \frac{V_{G1} \cdot F_{G1}^B + (V_{G2L}^B + FRC) F_{ET}^B}{V_A^B} \quad (6)$$

Equation (6) uses the fact that during steady-state $F_{ET}^k = F_{ET}^{k-1}$. On breath T0, a deviation from baseline is obtained by injecting a bolus of gas into $V_{G1}$ such that $F_{G1}^{T0} > F_{G1}^B$.

$$F_{AI}^{T0} = \frac{V_{G1} \cdot F_{G1}^{T0} + (V_{G2L}^{T0} + FRC) F_{ET}^B}{V_A^{T0}} \quad (7)$$

The task is to set $F_{G1}^{T1}$ such that $F_{ET}^{T1} = F_{ET}^{T0}$. For this to be true, a value of $F_{G1}^{T1}$ that ensures $F_{AI}^{T1} = F_{AI}^{T0}$ is searched. Assuming the correct value for $F_{G1}^{T1}$ is found, it is known that $FRC + V_{G2}$ contains neutral gas that doesn't contribute to the gas exchange, and this neutral gas will have a concentration $F_{ET}^{T0}$. The balance of gases may be re-examined during T0 and the gases may be redistributed for breath T1 such that $F_{AI}$ is the same but $F_{ET}$ is updated:

$$F_{AI}^{T0} = \frac{V_{G1} \cdot F_{G1}^{T1} + (V_{G2L}^{T0} + FRC) F_{ET}^{T0}}{V_A^{T0}} \quad (8)$$

If FRC is known, Equations (7) and (8) may be solved for $F_{G1}^{T1}$:

$$\frac{V_{G1} \cdot F_{G1}^{T1} + (V_{G2L}^{T0} + FRC) F_{ET}^{T0}}{V_A^{T0}} = \frac{V_{G1} \cdot F_{G1}^{T0} + (V_{G2L}^{T0} + FRC) F_{ET}^B}{V_A^{T0}} \quad (9)$$

$$\Rightarrow V_{G1} \cdot F_{G1}^{T1} = V_{G1} \cdot F_{G1}^{T0} + (V_{G2L}^{T0} + FRC) F_{ET}^B - (V_{G2L}^{T0} + FRC) F_{ET}^{T0}$$

$$\Rightarrow F_{G1}^{T1} = F_{G1}^{T0} - \frac{(V_{G2L}^{T0} + FRC)(F_{ET}^{T0} - F_{ET}^B)}{V_{G1}}$$

A study of equation (9) reveals that the gas concentration $F_{G1}^{T1}$ for subsequent breaths equals the gas concentration for the perturbation at T0 minus the change in the neutral volumes. The reduction reflects the contribution already present at the next breath.

Equation (9) has some interesting properties. When the end-tidal fraction does not change from baseline to T0, then $F_{G1}^{T1}$ becomes equal to $F_{G1}^{T0}$. Equation (9) does not relay on any assumptions regarding exchange with the capillary bed and does not require knowledge of the dissociation function. This formula is therefore true for two sequential breaths under SGD with constant $P_{\bar{v}}$ and can be expressed more generally:

$$F_{G1}^{k+1} = F_{G1}^k - \frac{(V_{G2L}^k + FRC^k)(F_{ET}^k - F_{ET}^{k-1})}{V_{G1}} \quad (10)$$

In equation (10), $FRC^k$ is the estimate for FRC on iteration k, and $F_{G1}^{k+1}$ is the estimated concentration for the next breath to return to steady state. The volume $V_{G1}$ of the first gas is expected to be constant between breaths, so it does not need to carry the indicia k in equation (10). Since the difference in successive values of $F_{ET}$ drives the adjustment of $F_{G1}$, it is safe to apply the update as long as $P_{\bar{v}}$ can be assumed constant, meaning that it can be applied on successive breaths to drive the system to steady-state. This is a feature of the present technology that allows accurate determination of CO with a single breath in most cases. Earlier systems may require at least 3 iterations, each iteration requiring 10 minutes.

It is expressed hereinabove that $F_{G1}^{T0}$ involves the injection of a bolus of gas. The principle works equally well when removing a bolus of gas, inasmuch as the steady state is momentarily disturbed after which a new steady-state is achieved.

Adaptation of FRC

Calculation of $F_{G1}^{k+1}$ depends on an accurate value for FRC. It may be observed that FRC is a quantity of interest in its own right, typically determined through a wash-out trial where the tidal volume is flooded with a single gas such as helium.

It might be possible to estimate FRC from the result at T0 if a reliable value for the change in gas-exchange with the blood was available. However, the best a-priori guess that may be produced is based on a current estimate of FRC, so that avenue is not useful unless some assumptions are made about the transport that occurs between alveolar space and the capillary bed.

After the gas exchange is complete an alveolar gas fraction of $F_{ET}^k$ may be observed. The volume of gas g exiting the body on exhale may be determined using equation (11):

$$V_g^k = V_{G1}(F_{ET}^k - F_{G1}^k) \tag{11}$$

Considering T0 when a bolus is injected, and T1 when $F_{G1}^{T1}$ is modified (usually reduced) to return the patient to steady state, a volume of gas exiting the patient may be calculating using equation (12) for T0 and equation (13) for T1:

$$V_g^{T0} = V_{G1}(F_{ET}^{T0} - F_{G1}^{T0}) \tag{12}$$

$$V_g^{T1} = V_{G1}(F_{ET}^{T1} - F_{G1}^{T1}) \tag{13}$$

Regardless of achieving return to steady state, $V_g^{T0}$ becomes much lower (for a bolus injection) than $V_g^{T1}$ because, at T0, gas is supplied to update the FRC as well. If the patient returns to steady state, i.e. if $F_{ET}^{T1} = F_{ET}^{T0}$, then equation (14) is verified:

$$V_g^{T1} - V_g^{T0} = \tag{14}$$
$$V_{G1}(F_{ET}^{T1} - F_{G1}^{T1}) - V_{G1}(F_{ET}^{T0} - F_{G1}^{T0}) = V_{G1}(F_{ET}^{T1} - F_{ET}^{T0} - F_{G1}^{T1} + F_{G1}^{T0}) =$$
$$V_{G1}(F_{G1}^{T0} - F_{G1}^{T1}) = FRC(F_{ET}^{T0} - F_{ET}^B)$$

Verifying equation (14) shows that to change the gradient in alveolar space from baseline with a perturbation in gas 1, the initial change adjusts both FRC and exchange with the capillary bed, while subsequent gas 1 fractions only needs to supply the capillary bed. Solving for FRC yields equation (15):

$$FRC = V_{G1} \frac{(F_{G1}^{T0} - F_{G1}^{T1})}{(F_{ET}^{T0} - F_{ET}^B)} \tag{15}$$

Equation (15) holds when the patient has returned to equilibrium. When equilibrium is not achieved, an unknown factor impacts gas exchange with the capillary bed. In practice, however, moderate changes in $F_{G1}$ during T0 result in minor changes in gas exchange to the capillary bed. Also, when the FRC estimate is reasonably close, the difference in $F_{ET}$ can be quite small and contributes relatively little.

Calculation of Cardiac Output

The cardiac output is calculated using the differential Fick equation (Equation (1)).

Calculation of Mixed Venous Gas Content

The mixed venous gas content ($C_{\bar{v}}$) is calculated the following equation (16):

$$C_{\bar{v}} = \frac{\dot{V}_g^k}{\dot{Q}_p} + F_{dis}(F_{ET}^k P_b)_{dis} \tag{16}$$

Wherein:
$\dot{V}_g^k$ is the mass balance for a gas g exiting the patient's body;
$\dot{Q}_p$ is the estimate of the CO; and
$F_{dis}(F_{ET}^k P_b)$ is the dissociation curve for gas b at the end-tidal fraction $F_{ET}^k$.

Implementation of the Algorithm

The algorithm first waits for end-tidal fractions to stabilize to establish baseline steady-state operation. This can be achieved, in a non-limiting example, by waiting for 10 minutes between measurements or monitoring end-tidal gas fraction. The criterion to establish the baseline steady-state operation is the stability of the end-tidal fractions and not the duration of this waiting time.

Figure 6:
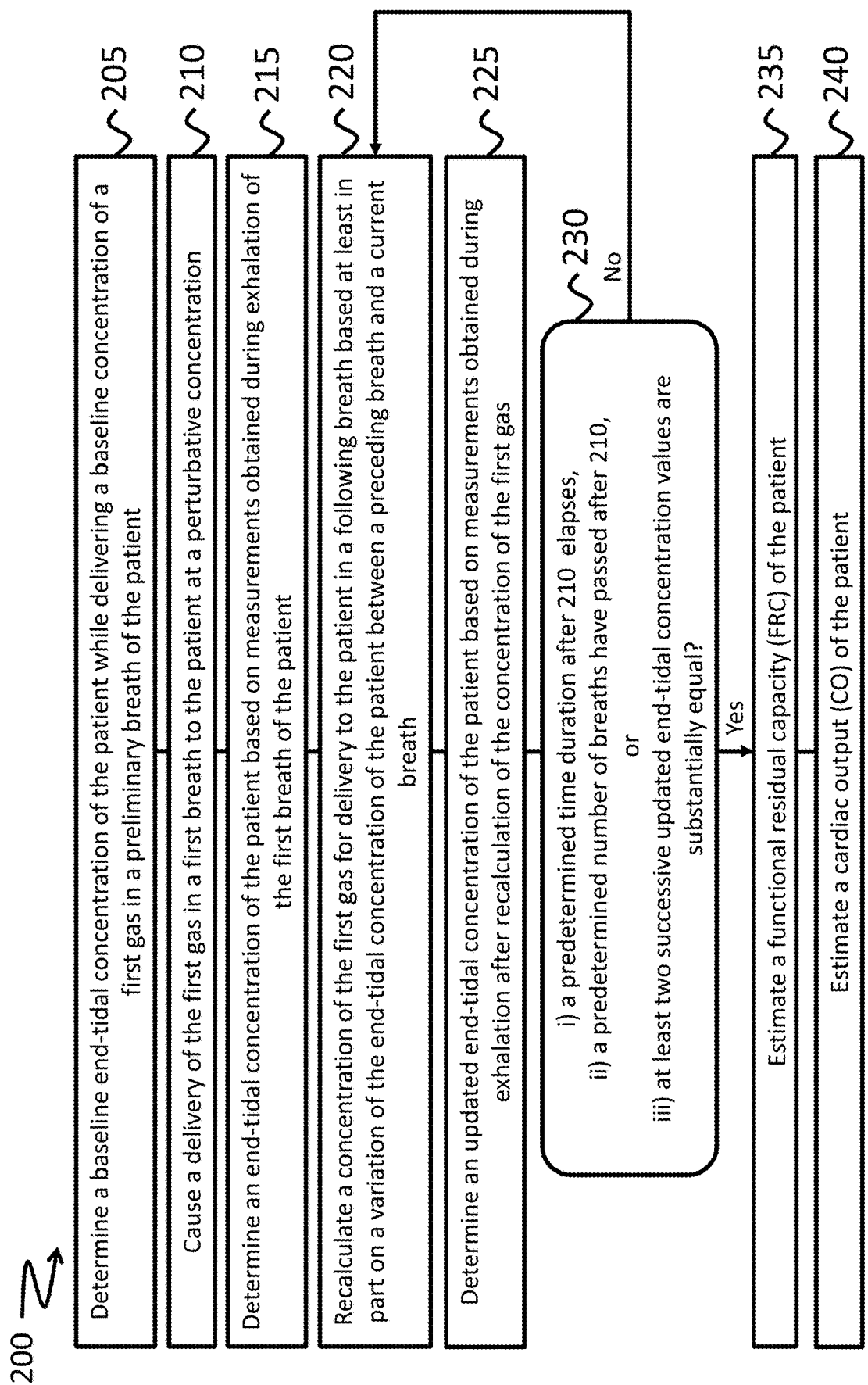
FIG. 6 is a sequence diagram showing operations of a method for estimating the efficiency of the lungs of a patient according to an embodiment.

FIG. 6 is a sequence diagram showing operations of a method for estimating the efficiency of the lungs of a patient according to an embodiment. On FIG. 6, a sequence 200 comprises a plurality of operations that may be executed in variable order, some of the operations possibly being executed concurrently, some of the operations being optional. The following operations are executed for subsequent breaths:

Operation 205: A baseline end-tidal concentration $F_{ET}^B$ of the patient may be determined while delivering a baseline concentration of a first gas $F_{G1}^B$ in a preliminary breath of the patient.

Operation 210: At a time T0, the first gas is caused to be delivered to the patient at a perturbative concentration $F_{G1}^{T0}$, thereby causing a perturbation of the gas delivery. At that time, a fixed-size perturbation is applied such that $F_{G1}^{T0} \neq F_{G1}^B$. The perturbation may for example be caused by delivering a bolus of gas to the patient.

Operation 215: Still at a time T0, an end-tidal concentration $F_{ET}^{T0}$ of the patient is determined based on measurements obtained during exhalation of the first breath of the patient.

Operation 220: At a time T1, the concentration of the first gas for delivery to the patient in a following breath is recalculated based at least in part on a variation of the end-tidal concentration of the patient between a preceding breath and the current breath. This recalculated concentration of the first gas $F_{G1}^{T1}$ may be calculated using equation (10). It may be observed that the concentration of the first gas may change or remain the same following this recalculation.

Operation 225: Still at a time T1, an updated end-tidal concentration $F_{ET}^{T1}$ of the patient is determined based on measurements obtained during exhalation after recalculation of the concentration of the first gas.

Operation 230: A test of three (3) criteria is made. It is determined whether at least one of at least one of i) a predetermined time duration after operation 210 elapses, ii) a predetermined number of breaths have passed after operation 210, or iii) at least two successive updated end-tidal concentration values are substantially. If the result is negative (none of the criteria is met), the sequence returns to operation 220. If the result is positive (at least one criterion is met), the sequence continues at operation 235.

Operation 235: The functional residual capacity (FRC) of the patient is estimated. Without limitation, the FRC may be estimated using equation (15).

Operation 240: The cardiac output (CO) of the patient may also be estimated. Without limitation, the CO may be estimated using equation (1).

Although not shown on FIG. 6, other events may take place within the sequence 200. Instead of or in addition to operations 235 and 240, the mixed venous gas content ($C_{\bar{v}}$) of the patient may be calculated, for example using equation (16). Also, the sequence 200 operates most efficiently when it is completed while blood flowing back to the lungs of the patient carries no significant trace of the gas delivered at the start of the sequence 200. Generally, the blood will circulate back to the lungs in about 20 seconds. For that reason, in a variant, the sequence 200 may be aborted if the test performed at operation 230 is still negative when 20 seconds have elapsed since the application of the perturbation at operation 210. The person of ordinary skill in the art will be able to adapt this 20-second duration to another predetermined time duration according to the clinical circumstances of the patient.

Alternate Implementation of the Algorithm

As an alternative to the sequence 200, the algorithm may be implemented as follows. The algorithm first waits for end-tidal fractions to stabilize to establish baseline steady-state operation. This can be achieved by waiting for 10 minutes between measurements or monitoring end-tidal gas fraction. Next, the following steps are executed for subsequent breaths:

1. Baseline, no perturbation;
   a. Record: $F_{ET}^{B}$, $F_{G1}^{B}$;
2. T0 (test 0): fixed-size perturbation is applied such that $F_{G1}^{T0} \neq F_{G1}^{B}$;
   a. Record: $F_{ET}^{T0}$, $F_{G1}^{T0}$;
3. Ti (test i): Update $F_{G1}$ according to Equation (10);
   a. Record: $F_{ET}^{Ti}$, $F_{G1}^{Ti}$;
4. Repeat step 3 until either:
   a. $F_{ET}^{Ti} = F_{ET}^{T(i-1)}$, or
   b. $F_{ET}^{Ti}$ is affected by recirculation
5. Update the estimates:
   a. Update FRC estimate using Equation (15); and
   b. Update CO estimate using Equation (1).

Figure 7:
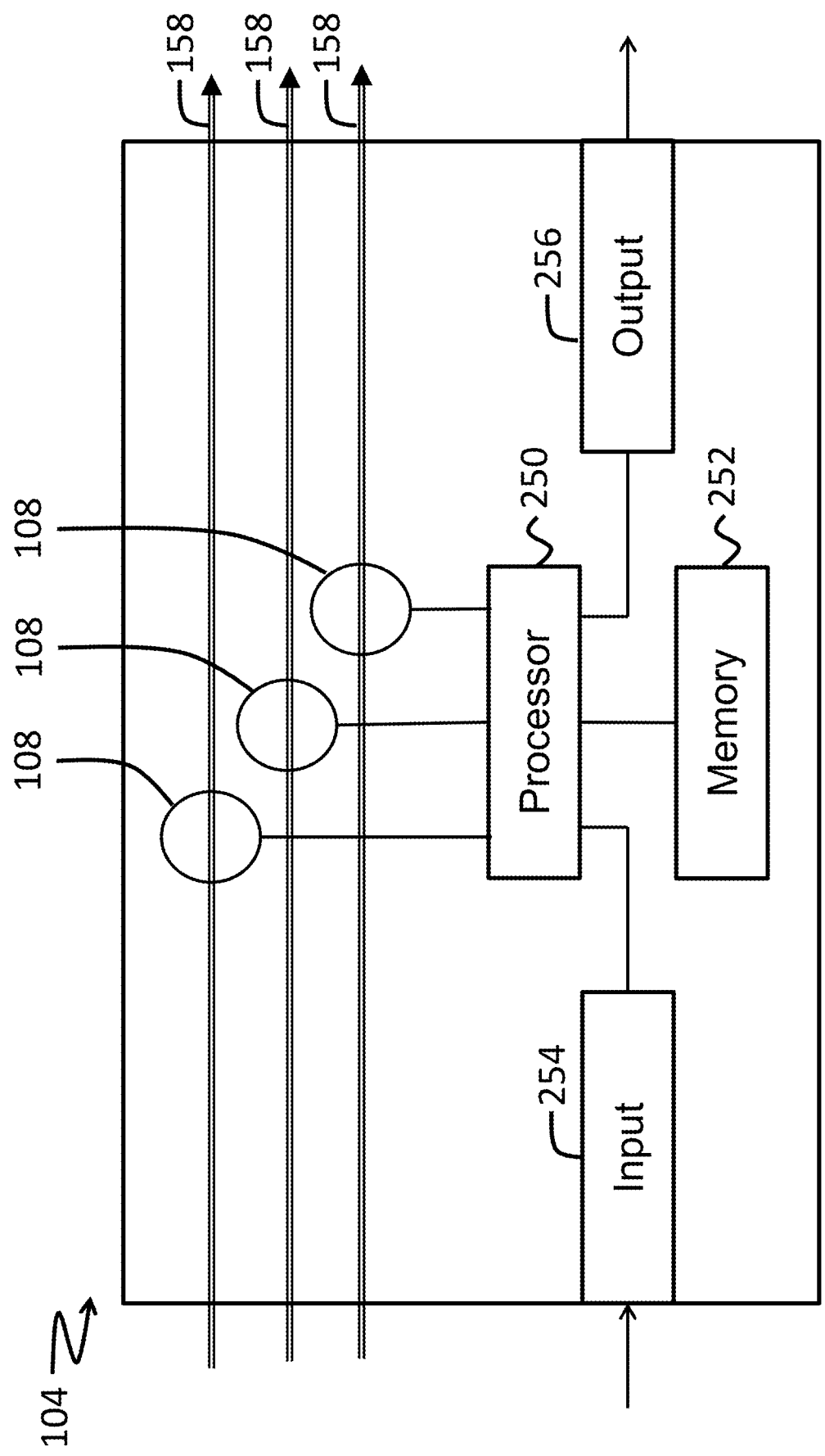
FIG. 7 is a block diagram of a controller part of the system of FIG. 1, according to an embodiment.

Each of the operations of the sequence 200 and each of the operations of the alternate Implementation of the algorithm may be configured to be processed by one or more processors, the one or more processors being coupled to a memory device. For example, FIG. 7 is a block diagram of the controller 104 part of the system 100 of FIG. 1, according to an embodiment. FIG. 7 is highly schematic and is not meant to provide an actual, physical representation of the controller 104. The skilled reader will be able to implement the features of the controller 104 based on the present disclosure. The controller 104 includes a number of internal valves 108 operative to allow or disallow delivery of gases from the challenge gas sources 114 through the conduits 158. Although three (3) internal valves 108 are shown on FIG. 7, the controller 104 may include a smaller or a larger number of internal valves 108. The controller 104 also includes one or more processors 250 (only one is shown) operatively coupled to the internal valves, to a memory device 252, to an input 254 and to an output 256. The processor 250 may receive, via the input 254, measurements from the gas composition sensor 116 and from the gas flow sensor 118 as well as commands from the operator interface 120. The processor 250 may forward, via the output 256, various physiological parameters from the gas composition sensor 116 and from the gas flow sensor 118 for showing on the display device of the operator interface 120. Although one processor 250, one memory device 252, one input 254 and one output 256 are shown on FIG. 7, an actual implementation may contain one or more of each of these components that together implement the features of the controller 104. The controller 104 may further include other components (not shown), including a power supply and ancillary equipment generally found on controllers and computer systems.

The processor 250 uses the measurements received from the gas composition sensor 116 and from the gas flow sensor 118 to control opening and closing of the internal valves 108 for the sequential delivery of gases to the patient 106. The memory device 252 may store in non-transitory fashion code instructions that, when executed by the processor 250, cause the controller 104 and the system 100 to perform the various operations of the sequence 200 illustrated on FIG. 6. Operational parameters received in commands from the operator interface 120 may be stored in the memory device 252 and used by the processor 250 to initiate or terminate the execution of the sequence 200. The same or additional operational parameters may be used for other purposes related to sequential delivery of gases to the patient 106, for example for selecting gases from one or more of the from the challenge gas sources 114.

Oxygen Delivery

The Cardiac Output being measured excludes blood flow not seen due to shunt. As such it is better characterized as Effective Pulmonary Flow as only this blood flow can be oxygenated. Since the end-tidal oxygen $F_{ET}O_2$ is known, the arterial oxygen content may be estimated and hence oxygen delivery. As shunt increases, however, the estimation of the arterial oxygen content may lose some precision. An alternate configuration would volumetrically estimate arterial oxygen content by differences between $F_{ET}O_2$ and fraction of inspired oxygen, $F_iO_2$.

Improved Time Resolution Using Multiple Gases

The method works for a plurality of distinct gas types, and the perturbation at T0 may be a sudden increase or a sudden decrease in gas fraction. $CO_2$, $O_2$, $N_2$, helium, or other gases may be used to cause the perturbation. Since perturbations of gases can be applied independently, time resolution can be increased by performing iterations with different gases in parallel at different moments in time.

Improved Accuracy Using Complementary Gases

When increasing delivery of a gas, for example, $CO_2$, the fraction of another gas, for example $O_2$, is reduced. The associated step change in the complementary gas can be analyzed in parallel to improve measurement resolution.

Tracking Changes in the Oxygen Dissociation Curve

With knowledge of the CO ($\dot{Q}_E$), determining points of the $O_2$ dissociation curve through application of the $CO_2$ dissociation curve may also be considered since the latter is less changeable.

Simulated Results

Figure 8A:
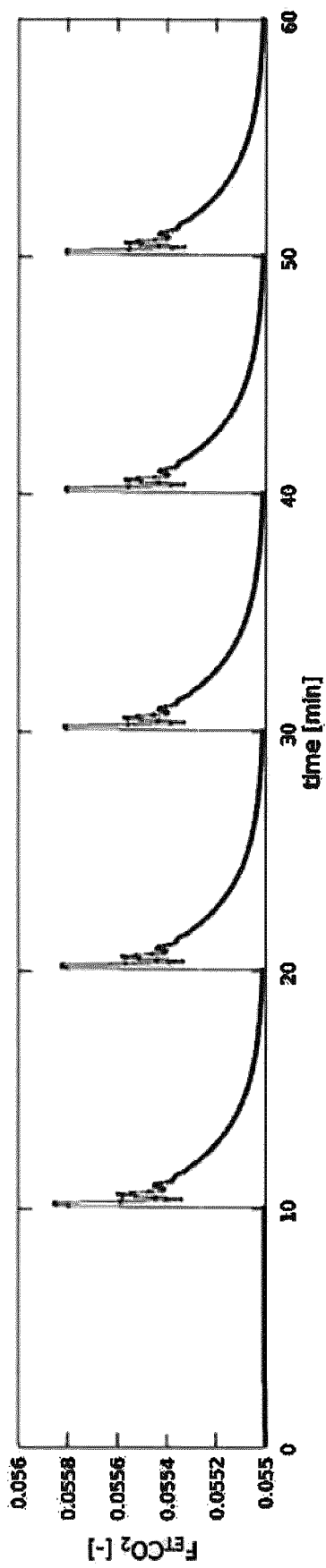
Figure 8B:
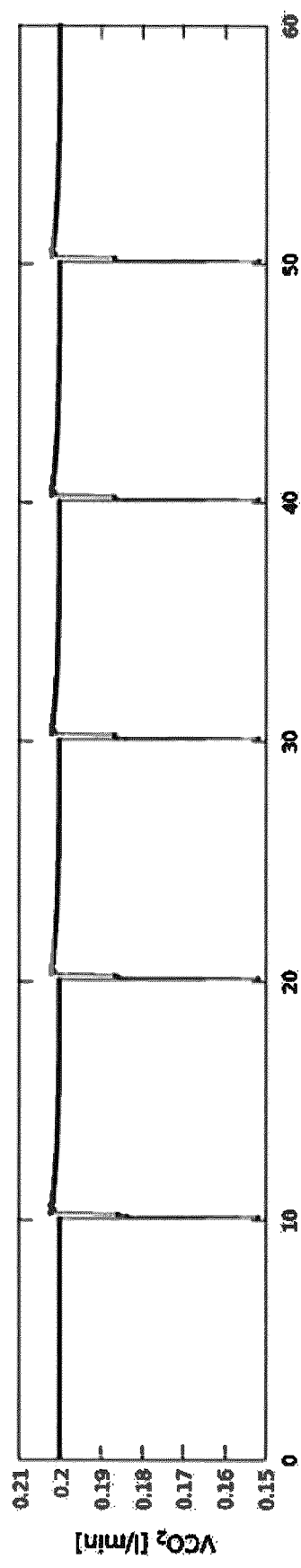

FIGS. 8a to 8d show 5 successive iterations of the algorithm. $CO_2$ is used as the gas for perturbation. In more details, FIG. 8a shows the variation of the end-tidal fraction $F_{ET}CO_2$ over time, FIG. 8a shows the variation of a volume of carbon dioxide used as a challenge gas over time, FIG. 8c shows a variation of the FRC over time, and FIG. 8d shows a variation of the CO over time. FIGS. 8a-8d share a common time scale. Ten minutes are required between iterations to allow the cardio-pulmonary system to return to steady-state. At each iteration four test breaths are applied (T0 to T3).

Figure 9A:
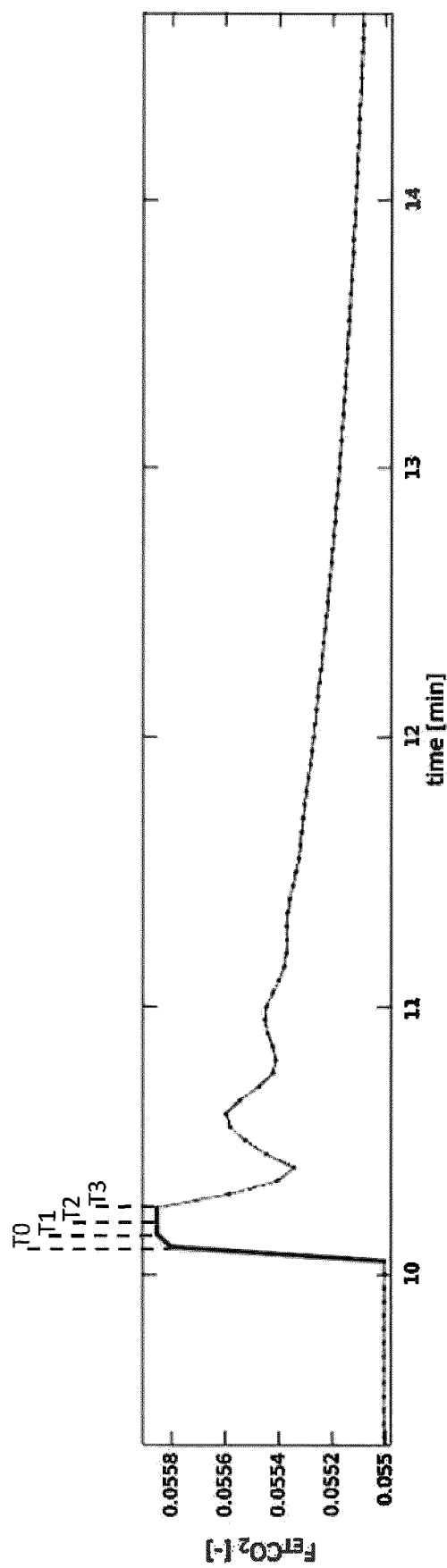
FIGS. 9a to 9d show details of the first iteration of FIGS. 8a to 8d.
Figure 9B:
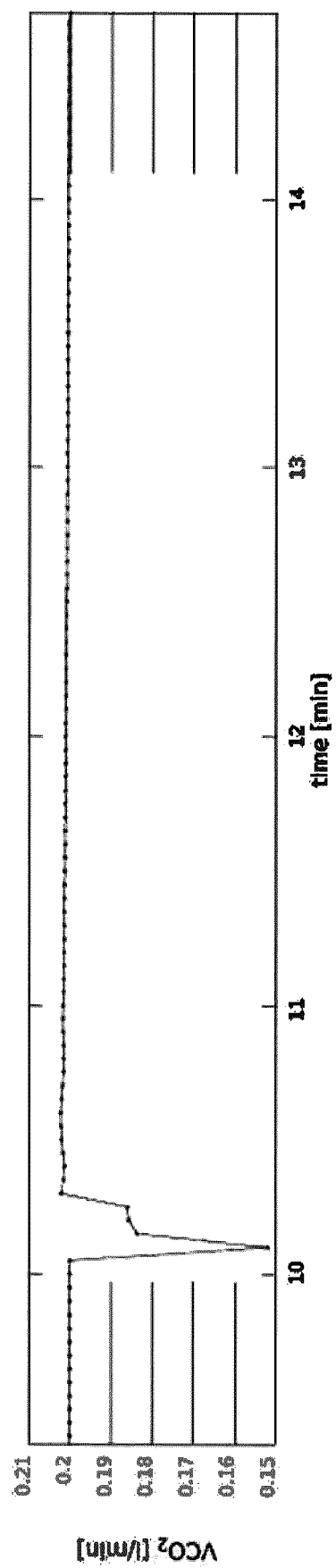
Figure 9C:
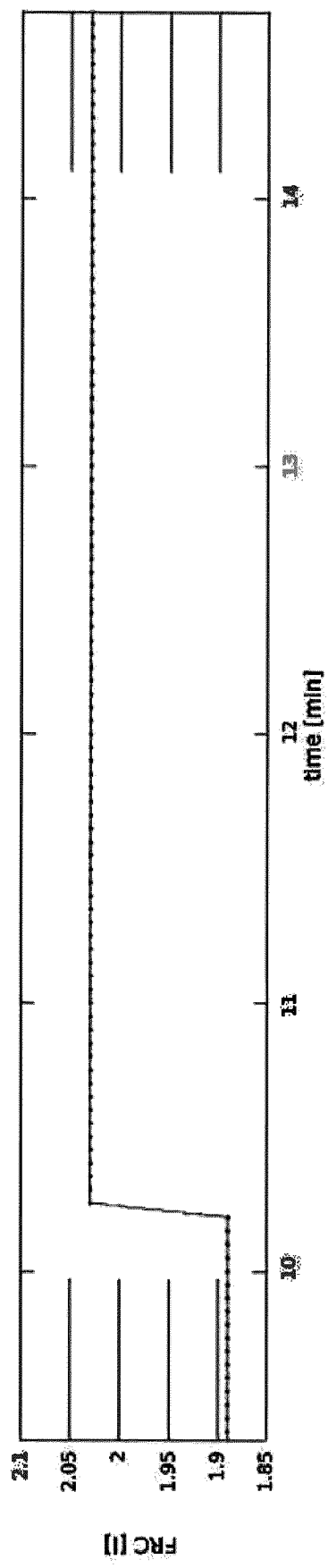
Figure 9D:
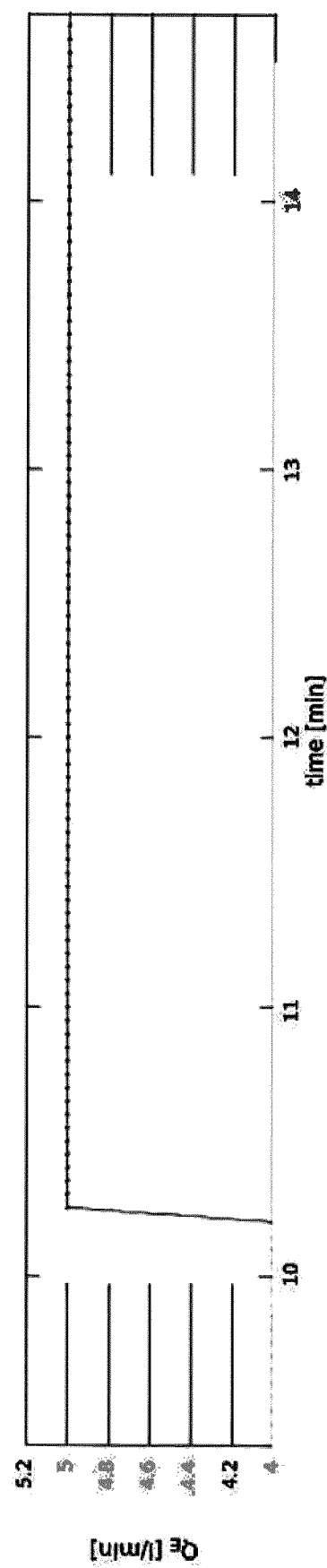

FIGS. 9a to 9d show details of the first iteration of FIGS. 8a to 8d. Curves on FIGS. 9a to 9d are for the same dimensions as for FIGS. 8a to 8d, however presented over a shorter time scale. Note that $F_{ET}CO_2$ increases from T0 to T1, indicating that the FRC estimate is incorrect and the patient does not return to steady-state immediately. FIG. 9a shows that, in a first exhalation, from T0 to T1, the end-tidal fraction $F_{ET}$ initially rises steeply without reaching a stable value. A small correction to the end-tidal fraction is needed in a subsequent exhalation. Repeated recalculation of $F_{G1}$ however manages to drive gas exchange back to steady-state by T3. As a result, convergence of CO is achieved in a single iteration.

Figure 10A:
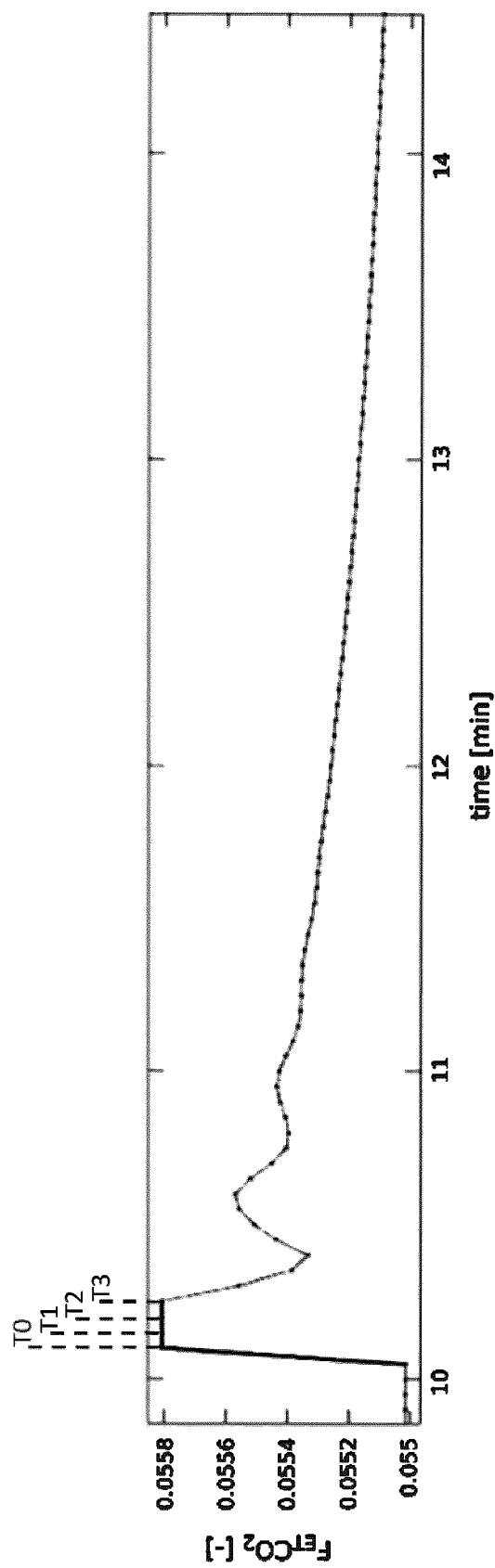
FIGS. 10a and 10b show details of a final iteration of the algorithm when both FRC and CO are known.
Figure 10B:
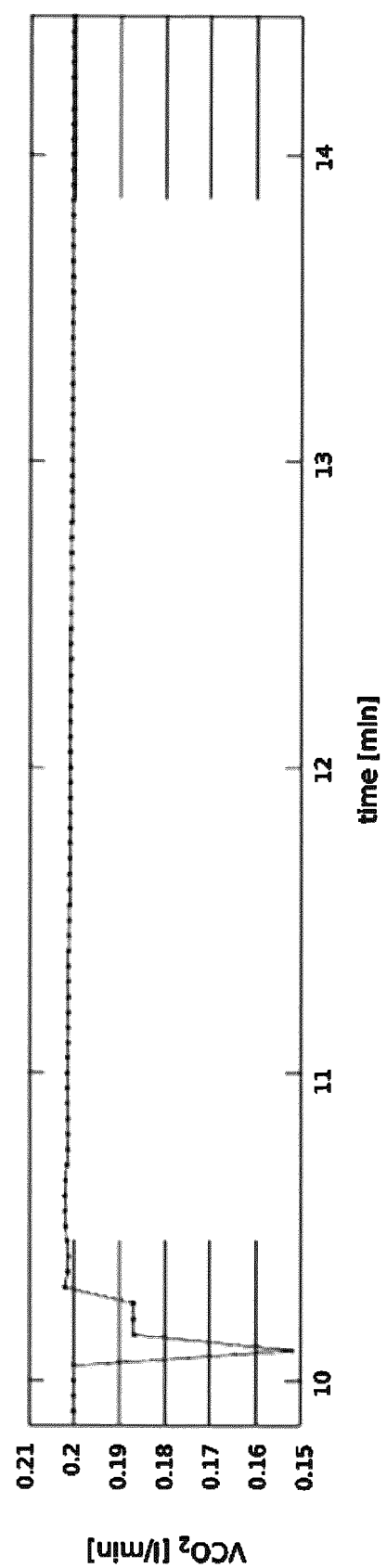

FIGS. 10a and 10b show details of a final iteration of the algorithm with correct estimates of both FRC and CO. $F_{ET}$ returns to steady-state immediately from T0 to T1, the first exhalation matching the second exhalation. With a simple criterion for steady-state, the number of test-breaths could be limited to two (2). This in turn reduces the recovery time between iterations, allowing increased sample speed. Chances of having to abort the sequence 200 of FIG. 6 are thus reduced.

Various embodiments of the present technology introduce a system that, through the control of the inhaled gas composition, returns the exhaled end-tidal concentration of a gas of interest to a steady state, after a perturbation has been delivered either from outside or within the body. To achieve the steady state, the desired inhaled concentration of the gas is calculated for breaths subsequent to the initial perturbation.

In some embodiments, the system is configured so that the desired inhaled concentration of the gas is calculated for breaths subsequent to the initial perturbation, without relying on an explicit knowledge of the Functional Residual Capacity (FRC) of the lungs of the patient.

In the same or other embodiments, the system allows to rapidly, estimate a cardiac output of the patient using an indirect differential Fick method to obtain a value of the cardiac output.

In the same or other embodiments, the system allows to return a respiratory state to an equilibrium after a perturbation. Then, an estimation is made of the FRC.

In the same or other embodiments, the system allows to determine the value of FRC with the use of plain gases, for example $O_2$, $CO_2$, or $N_2$. The system may use an adaptive method that does not require making unwarranted assumptions about the gas exchange that occurs in the blood.

In the same or other embodiments, the system uses knowledge of the FRC and achieves a return to steady-state in a single breath.

In the same or other embodiments, the system uses an end-tidal oxygen gas concentration sensor to determine the oxygen consumption ($VO_2$) by a patient.

In the same or other embodiments, the system combines multiple gases to improve the accuracy with which the lung's functions are elucidated, the improvements being for example in either the numerical or time-based accuracy of the determined parameters.

Those of ordinary skill in the art will realize that the description of the method and system for estimating the efficiency of the lungs of a patient are illustrative only and are not intended to be in any way limiting. Other embodiments will readily suggest themselves to such persons with ordinary skill in the art having the benefit of the present disclosure. Furthermore, the disclosed method and system may be customized to offer valuable solutions to existing needs and problems related to the titration of volumes (or flows) and concentration of supplied gases are adapted to the needs of each individual patient under respiratory care. In the interest of clarity, not all of the routine features of the implementations of the method and system are shown and described. In particular, combinations of features are not limited to those presented in the foregoing description as combinations of elements listed in the appended claims form an integral part of the present disclosure. It will, of course, be appreciated that in the development of any such actual implementation of the method and system, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of mechanical ventilation having the benefit of the present disclosure.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A method for estimating an efficiency of lungs of a patient receiving respiratory care, comprising:
   a) causing a delivery of a first gas in a first breath to the patient at a perturbative concentration;
   b) after a), determining an end-tidal concentration of the patient based on measurements obtained during exhalation of the first breath of the patient;
   c) recalculating a concentration of the first gas for delivery to the patient in a following breath based at least in part on a variation of the end-tidal concentration of the patient between a preceding breath and a current breath;
   d) determining an updated end-tidal concentration of the patient based on measurements obtained during exhalation after c);
   e) repeating c) and d) until at least one of:
      i) a predetermined time duration after a) elapses,
      ii) a predetermined number of breaths have passed after a), and
      iii) at least two successive updated end-tidal concentration values are substantially equal;
   f) after e), estimating a functional residual capacity (FRC) of the patient; and
   g) showing the estimated FRC of the patient on a display device.

2. The method of claim 1, wherein the further modified concentration of the first gas for delivery to the patient in the successive breath is calculated as:

$$F_{G1}^{k+1} = F_{G1}^k - \frac{(V_{G2}^k + FRC^k)(F_{ET}^k - F_{ET}^{k-1})}{V_{G1}}$$

wherein:

$F_{G1}^{k+1}$ is the further modified concentration of the first gas for delivery to the patient in the successive breath k+1;

$F_{G1}^{k}$ is a concentration of the first gas delivered to the patient in the current breath k;

$V_{G2}^{k}$ is a volume of a second gas delivered to the patient in the current breath;

$FRC^{k}$ is an estimate for the FRC for the current breath k;

$F_{ET}^{k}$ is the end-tidal concentration of the patient for the current breath k;

$F_{ET}^{k-1}$ is the end-tidal concentration of the patient for the preceding breath k−1; and $V_{G1}$ is a volume of the first gas delivered to the patient.

3. The method of claim 1, further comprising:
before a), determining a baseline end-tidal concentration of the patient while delivering a baseline concentration of a first gas in a preliminary breath of the patient;
wherein the FRC is estimated based on a volume of the first gas delivered to the patient, on recalculated concentration values of the first gas in last two instances of c), on successive updated end-tidal concentration values in the last two instances of d) and on the baseline end-tidal concentration of the patient.

4. The method of claim 3, wherein the FRC is calculated as:

$$FRC = V_{G1} \frac{(F_{G1}^{T0} - F_{G1}^{T1})}{(F_{ET}^{T0} - F_{ET}^{B})}$$

wherein:
$V_{G1}$ is the volume of the first gas delivered to the patient;
$F_{G1}^{T0}$ is the concentration of the first gas recalculated in a next to last instance of c);
$F_{G1}^{T1}$ is the concentration of the first gas recalculated in a last instance of c);
$F_{ET}^{T0}$ is the concentration of the end-tidal concentration in any one of the last two instances of d); and
$F_{ET}^{B}$ is the baseline end-tidal concentration of the patient.

5. The method of claim 1, further comprising estimating a pulmonary blood flow of the patient when at least two successive updated end-tidal concentration values are substantially equal.

6. The method of claim 5, further comprising calculating a mixed venous gas content of the patient.

7. The method of claim 6, wherein the the pulmonary blood flow is estimated using:

$$\dot{Q}_E = \frac{\dot{V}_g^B - \dot{V}_g^T}{F_{dis}(P_{ETg}^T) - F_{dis}(P_{ETg}^B)}$$

wherein:
$\dot{Q}_E$ is the estimate of the pulmonary blood flow when the mixed venous gas content is stable;
$\dot{V}_g$ is an amount of a gas g breathed out;
$P_{ETg}$ is a partial pressure of end-tidal g;
$F_{dis}(P_g)$ is a dissociation curve for gas g;
B designates baseline measurements obtained when determining the baseline end-tidal concentration of the patient; and T designates test measurements obtained after the baseline measurements.

8. The method of claim 1, wherein:
a second gas is delivered to the patient, an alveolar volume for a given breath of the patient being equal to a sum of (i) a volume of the first gas delivered in the given breath, (ii) a volume of the second gas delivered in the given breath and (ii) a value of the FRC during the given breath; and
the volume of the volume of the first gas delivered in the given breath and the volume of the second gas delivered in the given breath are sequential gas delivery (SGD) gas volumes.

9. The method of claim 1, wherein c) and d) are no longer repeated if two successive and substantially equal updated end-tidal concentration values are not obtained after a predetermined time duration after a).

10. A method for estimating an efficiency of lungs of a patient receiving respiratory care, comprising:
a) causing a delivery of a first gas in a first breath to the patient at a perturbative concentration;
b) after a), determining an end-tidal concentration of the patient based on measurements obtained during exhalation of the first breath of the patient;
c) recalculating a concentration of the first gas for delivery to the patient in a following breath based at least in part on a variation of the end-tidal concentration of the patient between a preceding breath and a current breath;
d) determining an updated end-tidal concentration of the patient based on measurements obtained during exhalation after c);
e) repeating c) and d) until at least one of:
i) a predetermined time duration after a) elapses,
ii) a predetermined number of breaths have passed after a), and
iii) at least two successive updated end-tidal concentration values are substantially equal;
f) after e), estimating a functional residual capacity (FRC) of the patient;
the method further comprising:
sensing a composition of gases inhaled or exhaled by the patient;
using a first composition sensor connected to an inhale limb connected to airways of the patient to sense the composition of gases inhaled by the patient; and
using a second composition sensor connected to an exhale limb connected to the airways of the patient to sense the composition of gases exhaled by the patient.

11. A method for estimating an efficiency of lungs of a patient receiving respiratory care, comprising:
a) causing a delivery of a first gas in a first breath to the patient at a perturbative concentration;
b) after a), determining an end-tidal concentration of the patient based on measurements obtained during exhalation of the first breath of the patient;
c) recalculating a concentration of the first gas for delivery to the patient in a following breath based at least in part on a variation of the end-tidal concentration of the patient between a preceding breath and a current breath;
d) determining an updated end-tidal concentration of the patient based on measurements obtained during exhalation after c);
e) repeating c) and d) until at least one of:
i) a predetermined time duration after a) elapses, ii) a predetermined number of breaths have passed after a), and iii) at least two successive updated end-tidal concentration values are substantially equal;

f) after e), estimating a functional residual capacity (FRC) of the patient;

the method further comprising:

sensing a flow of gases inhaled or exhaled by the patient;

using a first flow sensor connected to an inhale limb connected to airways of the patient to sense the flow of gases inhaled by the patient; and using a second flow sensor connected to an exhale limb connected to the airways of the patient to sense the flow of gases exhaled by the patient.

12. A system for estimating an efficiency of lungs of a patient receiving respiratory care, comprising:

at least one gas source;

a blender having a primary input port adapted to receive a first gas to be delivered to the patient and at least one secondary input port adapted to receive a second gas from a corresponding one of the at least one gas source, the blender further having a patient-side port adapted for delivery of the first gas and of the second gas from the at least one gas source toward the patient;

a gas composition sensor adapted to measure a fraction of the first gas;

a gas flow sensor adapted to measure a flow of the first gas; and a controller operatively connected to the at least one gas source, to the gas composition sensor and to the gas flow sensor, the controller being adapted to:

sequentially deliver the first and second gases to the patient, and estimate a functional residual capacity (FRC) of the patient based on measurements from the gas composition sensor and from the gas flow sensor;

wherein:

the gas composition sensor is a first gas composition sensor mounted on an inhale limb of a respiratory airway circuit connected to the patient and adapted to measure a composition of gases delivered to the patient;

the system further comprises a second gas composition sensor mounted on an exhale limb of the respiratory airway circuit and adapted to measure a composition of gases exhaled by the patient;

the gas flow sensor is a first gas flow sensor mounted on the inhale limb of the respiratory airway circuit and adapted to measure a flow of gases delivered to the patient; and the system further comprises a second gas flow sensor mounted on the exhale limb of the respiratory airway circuit and adapted to measure a flow of the gases exhaled by the patient.

13. The system of claim 12, wherein the controller is adapted modify the concentration of the first gas by controlling a delivery of the second gas from the at least one gas source to the blender.

14. The system of claim 12, wherein the controller comprises one of more valves adapted to control delivery of gases from corresponding ones of the at least one gas source toward corresponding ones of the at least one secondary input port of the blender.

15. The system of any one of claim 12, wherein the blender comprises:

an input side including the primary input port and the one or more secondary input ports; and an output side fluidly connected to the input side, the output side including a mixing chamber adapted to receive gases from the primary input port and from the one or more secondary input ports and to direct a blend of the received gases to the patient-side port.

16. The system of claim 15, wherein the mixing chamber is sized and configured to minimize dead space added by the blender in a respiratory airway circuit connected to the patient.

17. The system of claim 15, wherein the gas composition sensor and the gas flow sensor are mounted to the output side of the blender.

18. The system of claim 12, wherein the blender comprises:

an input side including the primary input port and the one or more secondary input ports; and an output side including:

a mixing chamber fluidly connected to the input side, the mixing chamber being adapted to receive gases from the primary input port and from the one or more secondary input ports and to direct a blend of the received gases to the patient-side port, and an exhaust port fluidly connected to the patient-side port and adapted to expel exhale gases received from the patient-side port.

19. The system of claim 12, wherein the primary input port of the blender is adapted to be connected to a mechanical ventilator for receiving therefrom the first gas to be delivered to the patient.

20. The system of claim 12, further comprising a mechanical ventilator fluidly connected to the primary input port of the blender.

21. A system for estimating an efficiency of lungs of a patient receiving respiratory care, comprising:

at least one gas source;

a blender having a primary input port adapted to receive a first gas to be delivered to the patient and at least one secondary input port adapted to receive a second gas from a corresponding one of the at least one gas source, the blender further having a patient-side port adapted for delivery of the first gas and of the second gas from the at least one gas source toward the patient;

a gas composition sensor adapted to measure a fraction of the first gas;

a gas flow sensor adapted to measure a flow of the first gas; and a controller operatively connected to the at least one gas source, to the gas composition sensor and to the gas flow sensor, the controller being adapted to:

sequentially deliver the first and second gases to the patient, and estimate a functional residual capacity (FRC) of the patient based on measurements from the gas composition sensor and from the gas flow sensor;

wherein the gas composition sensor comprises:

a pair of couplings mounted on the patient-side port of the blender and adapted for attachment of a pair of external optical fibers;

a light source adapted to illuminate a first one of the external optical fibers;

a first lens mounted on a first internal face of the patient-side port of the blender, the first lens being positioned to be illuminated by the first one of the external optical fibers;

a second lens mounted on a second internal face of the patient-side port of the blender, the second lens being positioned opposite from the first lens, light emitted by the first lens passing through a flow formed of the first and second gases before being received at the second lens to illuminate a second one of the external optical fibers; and a spectroscopic analyzer adapted to receive light from the second one of the external optical fibers and to provide the measure of the fraction of the first gas.

* * * * *